United States Patent [19]
Chandy et al.

[11] Patent Number: 5,827,655
[45] Date of Patent: Oct. 27, 1998

[54] ASSAY, METHODS AND PRODUCTS BASED ON N K$^+$ CHANNEL EXPRESSION

[75] Inventors: Kanianthara G. Chandy; Michael D. Cahalan, both of Laguna Beach, Calif.; Stephan Grissmer, Ulm, Germany; Alan L. Goldin, Irvine, Calif.; Brent A. Dethlefs, Laguna Niguel, Calif.; George A. Gutman, Costa Mesa, Calif.; John J. Wasmuth, Mission Viejo, Calif.

[73] Assignee: The Regents of the University of California, Oakland, Calif.

[21] Appl. No.: 527,152

[22] Filed: Sep. 12, 1995

Related U.S. Application Data

[60] Continuation of Ser. No. 170,418, Dec. 20, 1993, abandoned, which is a division of Ser. No. 558,568, Jul. 27, 1990, abandoned.

[51] Int. Cl.$^6$ .............................. G01N 33/53; C12Q 1/68
[52] U.S. Cl. .................................. 435/6; 435/7.6
[58] Field of Search .......................... 435/69.1, 6, 320.1, 435/240.2, 252.3, 254.11, 76

[56] References Cited

FOREIGN PATENT DOCUMENTS

| 89 06967 | 8/1989 | WIPO . |
| 89 06968 | 8/1989 | WIPO . |

OTHER PUBLICATIONS

Sands, et al. 1989. J. Gen. Physiol. vol. 93 pp. 1061–1074.
MacKinnon, et al. 1989. Science vol. 245, pp. 1382–1385.
Till, M.A., et al., "HIV–infected cells are killed by rCD4–ricia A chain", *Biological Abstracts*, 87(4):AB–167 (No. 34914) (1989).
Katz, F.E., et al., "Elimination of T cells from human peripheral blood and bone marrow using a cocktail of three and T–cell immunotoxins", *Biological Abstracts*, 85(7):AB–651 (No. 69872) (1988).
Theofilopoulos, A.N., et al., "Murine Models of Systemic Lupus Erythematosus", *Advance Immunology*, 47:269–390 (1985).
Shapiro, M.S., et al., "Two Types of Potassium Channels in a Lymphoma Cell Line", *Biophysical Journal*, 53:550a (1988).
Lewis, R.S., et al., "Subset–Specific Expression of Potassium Channels in Developing Murine T Lymphocytes", *Science*, 239:771–775 (1988).
DeCoursey, T.E., et al., "Mitogen Induction of Ion Channels in Murine T Lymphocytes", *The Journal of General Physiology*, 89;405–420 (1987).
Chandy, K.G, et al., "Altered K$^+$ Channel Expression in Abnormal T Lymphocytes from Mice with the lpr Gene Mutation", *Science*, 233:1197–1200 (1986).
Grissmer, S., et al., "Abundant Expression of Type 1 K$^+$ Channels, A Marker for Lymphoproliferative Diseases?", *The Journal of Immunology*, 141(4): 1137–1142 (1988).
DeCoursey, T.E., et al., "Voltage–gated K$^+$ channels in human T lymphocytes: a role in mitogenesis?", *Nature*, 307 (5950):465–468 (1984).
Wofsy, D., et al., "Successful Treatment or Autoimmunity in NZB/NZW F$_1$ Mice with Monoclonal Antibody to L3T4", *Journal of Experimental Medicine*, 161:378–391 (1985).
Wofsy, D., et al., "Treatment of Murine Lupus with Monoclonal Anti–T Cell Antibody", *The Journal of Immunology*, 134(2):852–857 (1985).
Santoro, T.J. et al., "The Contribution of L3T4$^+$ T Cells to Lymphoproliferation and Autoantibody Production in MRL–lpr/lpr Mice", *J. Exp. Med.*, 167:1713–1718 (1988).
Waldor, M.K., et al., "Reversal of Experimental Allergic Encephalomyelitis with Monoclonal Antibody to a T–Cell Subset Marker", *Science*, 227:415–417 (1985).
Ranges, G.E., et al., "Prevention of Type II Collagen–Induced Arthritis by In Vivo Treatment with Anti–L3T4", *J. Exp. Med.*, 162:1105–1110 (1985).
Christadoss, P., et al., "Immunotherapy for Myasthenia Gravis: A Murine Model", *The Journal of Immunology*, 136(7):2437–2440 (1986).
Wofsy, D., "Administration of Monoclonal Anti–T Cell Antibodies Retards Murine Lupus in BXSB Mice", *The Journal of Immunology*, 136(12):4554–4560 (1986).
Sainis, K., et al., "CD4$^+$ Cell Lines with Selective Patterns of Autoreactivity as well as CD4$^-$ CD8$^-$ T Helper Cell Lines Augment the Production of Idiotypes Shared by Pathogenic Anti–DBA Autoantibodies in the NZB X SWR Model of Lupus Nephritis", *The Journal of Immunology*, 140(7):2215–2224 (1988).
Shivakumar, S., et al., "Unusual T Helper Cells in Humans Augment the Production of Pathogenic Anti–DNA Autoantibodies", *FASEB J.*, 3:A492 (No. 1548) (1989).
Datta, S.K., et al., "Inductiion of a Cationic Shift in IgG Anti–DNA Autoantibodies", *J. Exp. Med.*, 165:1252–1268 (1987).
Miller, B.J., et al., "Both the LYT–2$^+$ and L3T4$^+$ T Cell Subsets are Required for the Transfer of Diabetes in Non-obese Diabetic Mice", *The Journal of Immunology*, 140(1):52–58 (1988).
Koike, et al., "Preventive Effect of Monoclonal Anti–L3T4 Antibody on Development of Diabetes in NOD Mice", *Diabetes*,36:539–541 (1987).
Tempel, B.L., et al., "Cloning of a probable potassium channel gene from mouse brain", *Nature*,332:837–839 (1988).

(List continued on next page.)

*Primary Examiner*—James Ketter
*Assistant Examiner*—Irem Yucel
*Attorney, Agent, or Firm*—Flehr Hohbach Test Albritton & Herbert LLP; Walter H. Dreger; Mark T. Kresnak

[57] ABSTRACT

This disclosure relates to the n K$^+$ channel expression product of the MK3 gene or a functionally bioactive equivalent thereof and its uses, particulary in combination with identifying immune responses and materials modulating or blocking same.

7 Claims, 8 Drawing Sheets

OTHER PUBLICATIONS

Baumann, A., et al., "Structure of the voltage–dependent potassium channel is highly conserved from Drosophila to vertebrate central nervous systems", *The EMBO Journal*, 7(8):2457–2463 (1988).

McKinnon, D., "Isolation of a cDNA Clone Coding for a Putative Second Potassium Channel Indicates the Existence of a Gene Family", *The Journal of Biological Chemistry*, 264(14):8230–8236 (1989).

Frech, G.C., et al., "A novel potassium channel with delayed rectifier properties isolated from rat brain by expression cloning", *Nature*, 340:642–645 (1989).

McCormack, T., et al., "Molecular cloning of a member of a third class of Shaker–family $K^+$ channel genes in mammals", *Proc. Natl. Acad. Sci. USA*, 87:5227–5231 (1990).

Ribera, A.B., "A Potassium Channel Gene is Expressed at Neural Induction", *Neuron*, 5:691–701 (1990).

Chandy, K.G., et al., "The Shaw–Related Ky3.1 Gene on Human Chromosome 11 Encodes the 1–Type $K^+$ Channel in T Cells", *Biophysical Journal*, 61(2):A257 (1484) (1992).

Grissmer, S., et al., "Expression and chromosomal localization of a lymphocyte $K^+$ channel gene", *Proc. Natl. Acad. Sci. USA*, 87:9411–9415 (1990).

Luneau, C.J., et al., "Alternative splicing contributes to $K^+$ channel diversity in the mammalian central nervous system", *Proc. Natl. Acadi. Sci. USA*, 88;3932–3936 (1991).

Murakami, M., et al., "In Vivo Effects of Tetraethylammonium (TEA), A $K^+$ Channel Blocker in MRL/lpr Mice", *The FASEB Journal*, p. A2108 (No. 2404) (1990).

Chandy, K.G., et al., "Altered $K^+$ Channel Expression in T Cells: A Molecular Feature Unique to Murine SLE and Type–1 Diabetes", *American Rheumatism Association*, 53rd Annual Scientific Meeting, Cincinnati, Ohio (1989).

Chandy, K.G., et al., "The MBK1 mouse $K^+$ channel protein is encoded by a single uninterrupted exon", *Society for Neuroscience Abs.*, vol. 15 (No. 230.1) (1989).

Grissmer, S., et al., "$CD4^-$ $CD8^-$ T Cells from Mice with Collagen Arthritis Display Aberrant Expression of Type 1 $K^+$Channels", *The Journal of Immunology*, 145(7):2105–2109 (1990).

Mathew, M.K., et al., "Cloning and characterization of human potassium channel genes", *Society for Neuroscience Abstracts*, 15(1):540 (No. 220.12) (1989).

Ramaswami, M., et al., "Human Potassium Channel Genes: Molecular Cloning and Functional Expression", *Molecular and Cellular Neurosciences*, 1:214–223 (1990).

Yokoyama, S., et al., "Potassium channels from NG108–15 neuroblastoma–glioma hybrid cells, Primary structure and function expression from cDNAs", *FEBS Letters*, 259(1):37–42 (1989).

Grupe, A., et al., "Cloning and expression of a human voltage–gated potassium channel. A novel member of the RCK potassium channel family", *The EMBO Journal*, 9(6):1749–1756 (1990).

Chandy, K.G., et al., "A Family of Three Mouse Potassium Channel Genes with Intronless Coding Regions", *Science*, 247:973–975 (1990).

Chandy, K.G., et al., "Multiple Genes Contribute to $K^+$ Channel Diversity in the Mouse KG", *Abtract Submission*, Baltimore.

Grissmer, S., et al., "Does the MK3 Gene Encode the Voltage–Gated Type n $K^+$ Channel in T Lymphocytes?", *International Biophysical Congress*, Vancouver, Canada (1990).

Douglass, J., et al., "Characterization and Functional Expression of a Rat Genomic DNA Clone Encoding a Lymphocyte Potassium Channel", *The Journal of Immunology*, 144(12):4841–4850 (1990).

Stühmer, W., et al., "Molecular basis of functional diversity of voltage–gated potassium channels in mammalian brain", *The EMBO Journal*, 8(11):3235–3244 (1989).

Swanson, R., et al., "Total Synthesis, Expression, and Functional Assay of a Gene Encoding a Human Delayed Rectifier Potassium Channel", *Biophysical Journal*, 57:211a (1990).

Miller, R.J., "Glucose–regulated potassium channels are sweet news for neurobiologists", *Trends in Neuroscience*, 13(6):197–199 (1990).

Cook, N.S., "The pharmacology of potassium channels and their therapeutic potential", *TIPS*, 9:21–28 (1988).

Robertson, D.W., et al., "Potassium Channel Modulators: Scientific Applications and Therapeutic Promise", *Journal of Medical Chemistry*, 33(6):1529–1541 (1990).

Swanson, R., et al., "Cloning and Expression of cDNA and Genomic Clones Encoding Three Delayed Rectifier Potassium Channels in Rat Brain", *Neuron*, 4:929–939 (1990).

Chandy, K.G., et al., "Autoimmune diseases linked to abnormal $K^+$ channel expression in double–negative $CD4^-CD8^-$ T cells", *Eur. J. Immunol.*, 20:747–751 (1990).

Ghanshani, S., et al., "Mouse Genomic Clones Encoding Shaker–and Shaw–Related Voltage–Gated $K^+$ Channel Genes", *Abstract Submitted for Biophysics Conference*, Vancouver, (1990).

Gupta, S., "Autologous Mixed–Lymphocyte Reaction in Man, XVII, In Vitro Effect of Ion Channel–Blocking Agents on the Autologous Mixed–Lymphocyte Response", *Cellular Immunology*, 104:290–295 (1987).

Schell, S.R., et al., "The Inhibitory Effects of $K^+$ Channel–Blocking Agents on T Lymphocyte Proliferation and Lymphokine Production are 'Nonspecific'", *The Journal of Immunology*, 139(10):3224–3230 (1987).

DeCoursey, T.E., et al., "Two Types of Potassium Channels in Murine T Lymphocytes", *J. Gen. Physiol.*, 89:379–404 (1987).

Gutman, G.A., et al., "Nomenclature of mammalian voltage–dependent potassium channel genes", *The Neurosciences*, 5:101–106 (1993).

Attali, B., et al., "Cloning, Functional Expression, and Regulation of Two $K^+$ Channels in Human T Lymphocytes", *The Journal of Biological Chemistry*, 267(12):8650–8657 (1992).

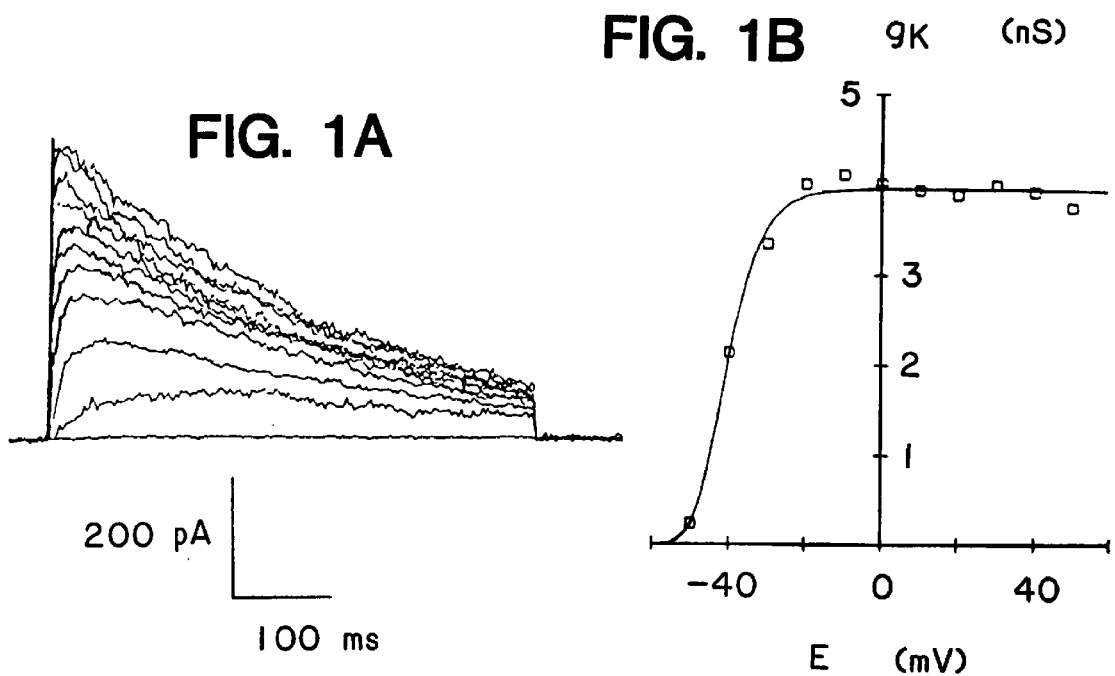
FIG. 1A
FIG. 1B
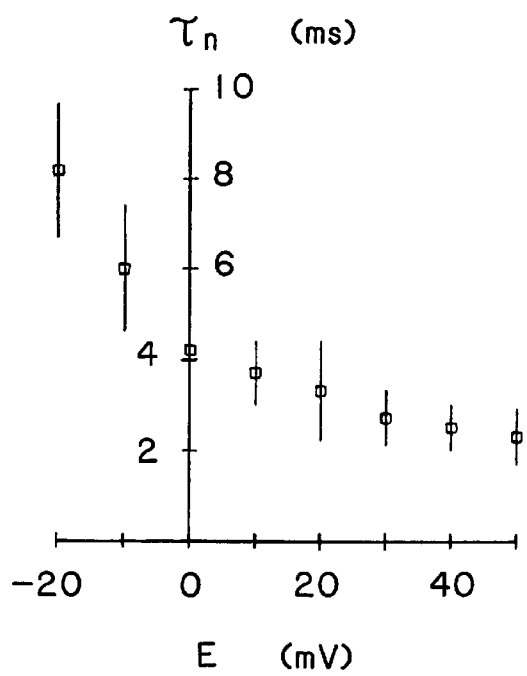
FIG. 1C
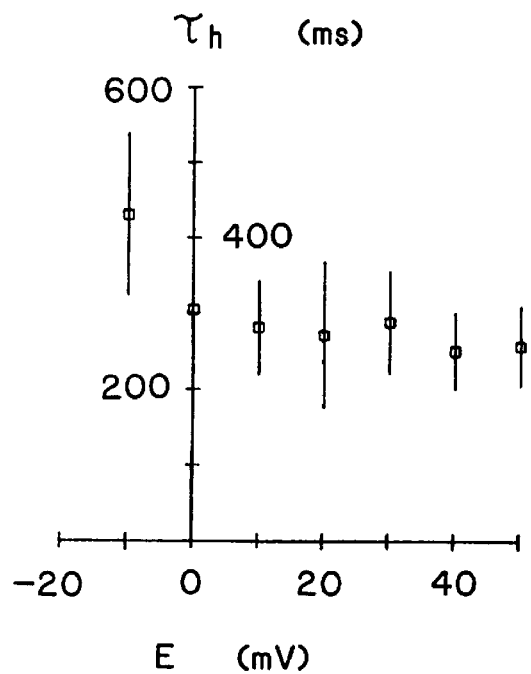
FIG. 1D

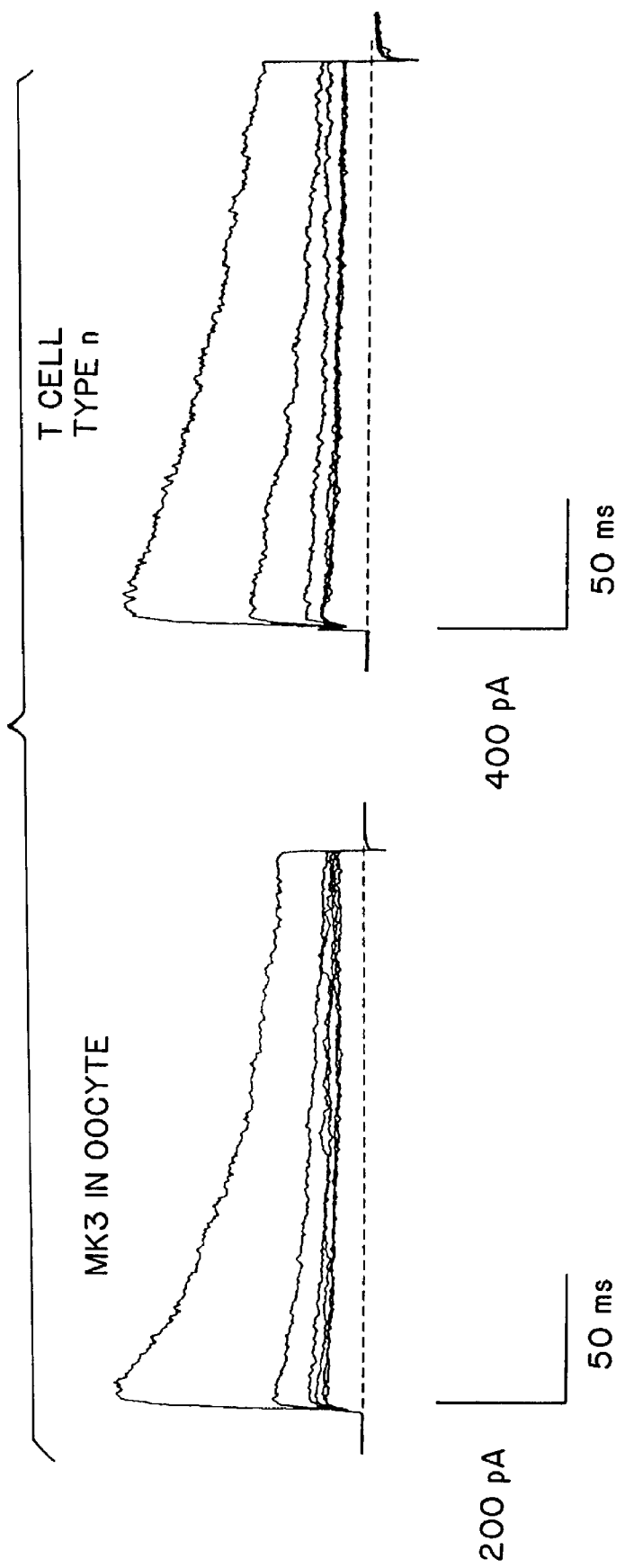

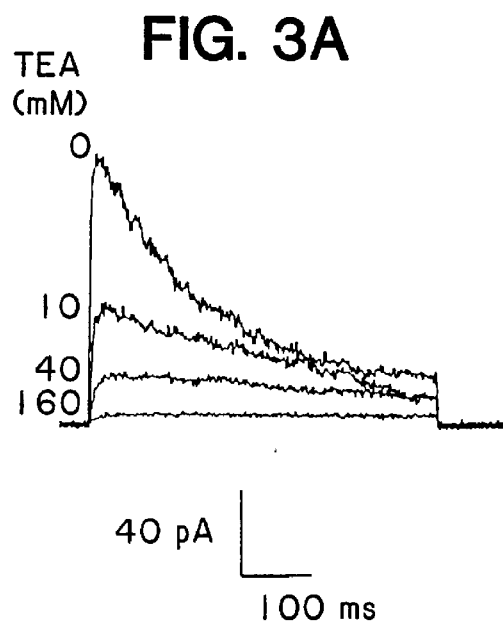
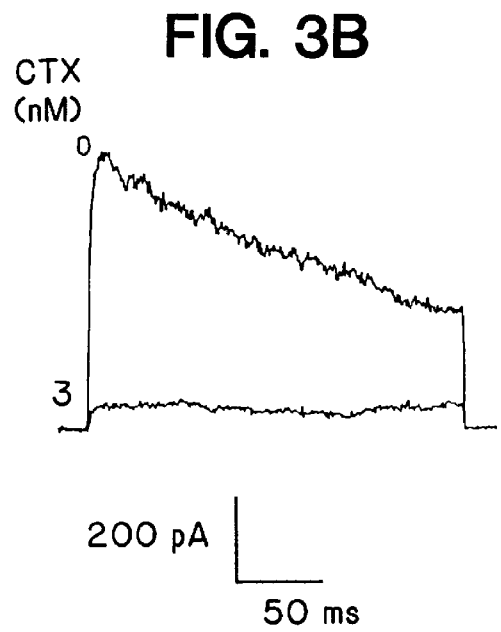
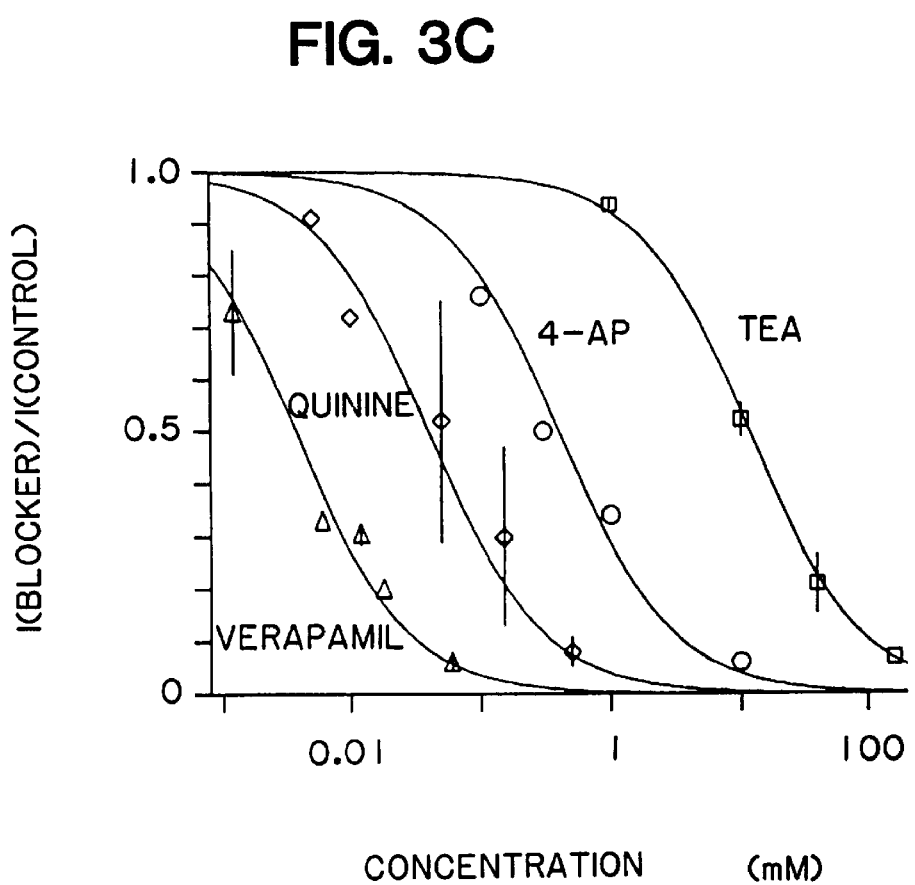

FIG. 5

| CELL LINE | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y | MK2 | MK3 |
|---|---|---|---|---|---|---|---|---|---|---|---|---|---|---|---|---|---|---|---|---|---|---|---|---|---|---|
| CHO | | | | | | | | | | | | | | | | | | | | | | | | | | |
| 151 | | | | | | + | | | | | | + | | | | | | | | | | | | | + | |
| 212 | | | | | d | | | | | | | | | | | | | | | | | | | + | | |
| 324 | | | | | | | | | | | | | | | | | | + | | | | | | | | |
| 339 | | | | + | d | ★ | | | | | | + | | | + | + | | + | | + | + | | | | + | |
| 423 | | | + | | | | | | | | | | | | | | | | | | | | | | | |
| 484 | | | | | + | | | | | | | P | | | | | | | | | | | | | | |
| 488 | | + | + | | + | | | | | | | | + | | | | | + | | | | | | | | |
| 660 | | + | P | d | | | | | + | | | | + | | + | | | + | | | | | | | | |
| 671 | | | + | + | ★ | | | | | | | + | | | | | ★ | | + | | + | | | | + | |
| 724 | | + | | d | + | | | | + | | | | | + | | | Q | | + | | | | | | | |
| 734 | | | + | | | | + | | | | | | | | | | + | | | | | | | | | |
| 735 | | | + | | | + | + | | | | | | | | | | + | | | | + | | | | | |
| 750 | | | d | | | | | | | | | ★ | + | + | | | | + | | | | | | | | + |
| 751 | | | + | + | | | | | | | | ★ | | | | | | | + | | | | | | | |
| 803 | | | + | + | | + | | | | | | | | | | | | | | | + | | | | | |
| 811 | | | | | + | | | | | | | | | | | | + | + | | | | | | | | |
| 854 | | ★ | | + | | | | | | | | | | | | | | | | | | | | | | |
| 860 | | + | + | + | | + | | | | | | | | | | | + | | + | | | | | | | |
| 861 | | + | + | | | + | | | | | | | | | | | + | | | | | | | | | |
| 862 | | | + | | | + | | | | | | | | | | | | | | | | | | | | |
| 863 | + | | + | + | | + | | | + | + | + | + | | | | | | + | ★ | + | + | + | | | + | |
| 864 | | | + | + | | | ★ | | + | | | | | | | | + | | | + | | | | | + | + |
| 867 | + | | | + | | | | | | | + | + | | ★ | | + | + | | | | | | | | | + |
| 906 | | + | + | | | | | | | | | + | | | | | | + | | | | | | | | |
| 908 | | + | + | + | | | | | | | | ★ | | | | | + | | + | | | | | | | |
| 909 | | d | + | + | | | | | | | | + | | | | | | | + | | | | | | | |
| 937 | + | | + | | | | | | | | + | + | | + | | | + | | | | | | | | | |
| 940 | | | + | | | | | | | | | | | | | | | | | + | | | | | | |
| 686 | | | + | | | | | | | | | + | | | | | | | | | | | | | | + |

DISCORDANT 22
MK2  8 6 10 4 11 2 11 6 5 8 0 9 12 7 5 7 10 11 7 10 5 6 6
MK3  4 4 9 7 22 9 7 10 6 7 8 9 0 7 6 8 6 10 10 6 11 8 7 6

FIG. 6

MK3 NUCLEOTIDE SEQUENCE FROM GenBank ENTRY

```
   1 agccgcgct agggaaggaa agcaccgcgg cctcccgccg tcgaccgccg cagccctcca
  61 cccatcaccg cgcccaccct gcaccggacc ccgcaggagg cggcgcgcgc atcctgcaga
 121 gccccggcca cgccgagctg ccgccagaca tgaccgtggt gccgggggac cacctgctgg
 181 agccagaggc ggcggaggc ggtggcgggg acccgcctca gggaggctgt ggcagtggcg
 241 gcggcggtgg cgcctgcgac cgctacgagc cactgccacc cgcgctgccc gccgcggggcg
 301 agcaagattg ctgcggcgag cgtgtggtca tcaacatctc cgggctgcgc ttcgagacgc
 361 agctcaagac ccctctgcca ttccccgaga cactgctggg cgaccccaag cggcgcatgc
 421 gtactttga cccactccgc aatgagtact tcttcgaccg caaccgaccc agcttcgacg
 481 ccatcctcta ctactaccag tccgggggcc gcattcgccg gcggtcaac gtgccatcg
 541 acatcttctc cgaggagatc ggcttttacc agctggtga ggaggccatg gaaaagttcc
 601 gtgaggatga gggcttcctg cgggaggagg agccgaccct gccccgccgt gacttccagc
 661 gccaggtgtg gctgctcttc agcctcccgg agagctccgg gcggcccggg gcattgccaa
 721 ttgtgtcagt gctgtcatt ctcatctcca ttgtcatctt ctgcttggag acgcttcccg
 781 agtttcgcga tgagaaagac tatcccgcct ccccgtcgca ggacgtgttt gaggctgcca
 841 acaacagcac gtcgggggcc cctctggag ctcgagctt ctcggacccc ttcttcgtgg
 901 tggagacctt gtgcatcatc tggttctcct ttgagcttct ggtgcgttc tttgcttgcc
 961 ccagtaaagc caccttctcc agaaatatca tgaacttgat agacattgtg gccatcattc
1021 cttattttat cactctgggc actgagctgg ctgaacgaca aggtaatggg cagcaggcca
1081 tgtcgctggc catcctaaga gtcatccgcc tagtaaggtt tttccgcatc ttcaagctct
1141 cccgccattc taagggctg cagatcctag gacagacgct gaaggcttcc atgcgggagc
1201 tgggctgct catattcttc ctcttcattg ggtcatcct tttctccagt gcagcttact
1261 ttgctgaggc agacgaccct tcttcgggtt ttaacagtat ccggatgcc ttctgtggg
1321 cagtagtaac catgacaaact gttggttatg gtgatatgca cccagtgacc ataggaggca
1381 agattgtggg ctctctttgt gccatcgcag gtgtcttgac cattgcattg ccagttcctg
1441 tgattgtttc caacttcaac tacttctacc accggagac agaagggaa gagcaagccc
1501 agtacatgca cgtgggcagt tgccagcacc tctcctcttc agccgaggag ctccgaaaag
1561 ccggagtaa ctccactctg agtaagtcgg agtatatggt gatcgaagag gggggtatga
1621 accagagcgc cttcccgcag acccccttca aacgggcaa ctccacagcc acttgcacca
1681 cgaacaataa cccaactcc tgtgtcaaca tcaagaagat attcactgat gtctaatata
1741 tgatacggtt gccaattctg tgcccagtat tgtgtggaac atgcccctt ggtctgtgta
1801 tgcccttgat ttatacattt ccagaccact catcaaggaa agtacaagaa gtgaggaagc
1861 acacttcatt ctccctattg cttcatactg aacaggtgc ctgttttgc aagtggctg
1921 cattctctca gctcttttt tctctctctc cctgtctctt aattttgtga ccaacaaact
1981 tacattaagc gtgg
``` ize=5,827,655

ASSAY, METHODS AND PRODUCTS BASED ON N K⁺ CHANNEL EXPRESSION

CROSS-REFERENCE TO RELATED APPLICATIONS

This is a continuation of U.S. Ser. No. 08/170,418, filed 20 Dec. 1993, now abandoned which is a divisional of U.S. Ser. No. 07/558,568 filed 27 Jul. 1990 now abandoned.

ACKNOWLEDGMENT

This invention was made with U.S. Government support under Grant Nos. AI24783, AI21366, NS26729, NS14609, and GM 42365 awarded by the National Institutes of Health. The Government has certain rights in this invention.

FIELD OF THE INVENTION

The present invention relates generally to advances in the field of cell physiology, specifically, physiologic and recombinant DNA methods useful to characterize cell function and physiology. Particularly, the present invention relates to the molecular identity of a particular trans-membrane ion channel, the definition of the channel's biophysical properties, the expression product of the gene which codes for the channel and uses of same. More particularly, the present invention arises in part from the determination that the DNA sequence of the MK3 gene encodes the type $\underline{n}$ K⁺ channel in T-lymphocytes.

BACKGROUND OF THE INVENTION

The membranes found at the surface of mammalian cells perform functions of great importance relating to the integrity and activities of cells and tissues. Of particular interest is the study of ion channel biochemistry, physiology, pharmacology and biokinetics. These ion channels, which include sodium (Na), potassium (K) and calcium (Ca) channels are present in all mammalian cells and control a variety of physiological and pharmacological processes. Particular attention has been focused on the potassium channel, particularly its involvement in normal cellular homeostasis and its possible association with and derangements relating to a variety of disease states and immune responses. Considerable research has been expended and is currently underway in order not only to devise a treatment or prophylaxis against such devastating diseases, but also to study the underlying etiology(ies) such that a better understanding can be gained as to common denominators, if any, that would more directly focus a plan of attack for conquering them. Diseases having a particular association with such channels include autoimmune diseases and other proliferative disorders such as cancers. Autoimmune diseases include rheumatoid arthritis, type-1 diabetes mellitus (insulin dependent), multiple sclerosis, myasthenia gravis, systematic lupus erythematosus, Sjogren's syndrome, mixed connective tissue disease, experimental allergic encephalomyelitis (EAE), to name a few.

In most cases, it is believed that autoimmune diseases result from abnormal cells of the immune system destroying target tissues, either by direct killing or by producing autoantibodies. One may focus for exemplification on historic autoimmune diseases. One such is the so-called systematic lupus erythematosus (SLE). In SLE, abnormal b-lymphocytes produce anti-DNA antibodies that are positively charged and aggregate on negatively charged kidney cells causing inflammation and nephritis, which is symptomatic of SLE. In diabetes mellitus, abnormal T cells systematically destroy pancreatic islet cells such that they prove incapable of producing insulin, a necessary hormone for proper metabolic balance in an organism. In multiple sclerosis, abnormal T cells are believed to damage myelin basic protein, a major component of nerve cells, which systematically destroys certain nerve cells, causing a spectrum of neurological symptoms. In the autoimmune diseases studied to date, there seems to emerge a common pattern of abnormal immune system cells producing materials that either destroy or retard certain target tissues causing symptoms manifest for that disease state.

Additionally, allografts or xenografts may be rejected through either a cell-mediated or a humoral immune reaction of the recipient against antigenic components present on the donor's cell membranes. The principal mechanism of rejection is the acute lymphocyte-mediated immune reaction against transplantation antigens (host-vs.-graft reaction). Particular focus in immunobiologic rejection has been to determine means of assessing responses to treatment and to diagnose rejection prior to functional deterioration of the graft. However, completely reliable and reproducible methods of monitoring immune responses remain to be established.

Additionally, other cell-proliferative conditions, particularly those relating to cancer and tumoricity, may also have a like association with immunologic factors. For instance, host-tumor immunologic factors play a role in the clinical course of malignant lesions. Both humoral and cellular expression of immunoincompetence in patients with sarcomas have been reported. Additionally, correlations have been shown between the degree of general depression of immunologic responsiveness and the subsequent clinical progression of disease. However, the routine use of immunologic monitoring remains experimental and its clinical usefulness as yet undetermined.

Current treatment for these responses and diseases remains on an empirical level and is based on causing generalized immunosuppression, either with steroids or other immunosuppressive drugs. This therapeutic approach is also fraught with other problems including associated severe side effects. Further, they serve only to retard the natural progression of these autoimmune diseases. Effective therapeutic treatment, to say nothing of a cure, is beyond present day medical technology. The aberrations in the immune system resulting in these various autoimmune diseases, immune responses and tumorality are not well understood, despite the extensive research that has taken place in this field. See Theofilopoulos, et al., *Adv. Immunol.* 37, 269 (1985), for example.

Research has focused on the use of various murine models that have provided considerable insight into the pathogenesis of the disease states, although the clinical syndromes and immunological abnormalities vary considerably from strain to strain, making them less than perfect studies. Thus, a common underlying cellular or molecular defect that is common to all these diseases has not been identified, if indeed there is even a suggestion in the extant art that one exists.

Several classes of K⁺ channels are involved in maintaining membrane potential and regulating cell volume in diverse cell types, as well as modulating electrical excitability in the nervous system (1). Potassium channels have been shown to control the repolarization phase of action potentials and the pattern of firing neurons and other cells. Potassium currents have been shown to be more diverse than sodium or calcium currents, and also play a central role in determining the way a cell responds to an external stimulus. For instance, the rate of adaptation or delay with which a neuron responds to synaptic input is strongly determined by the presence of different classes of $K^+$ channels. The molecular mechanisms generating $K^+$ channel diversity are best understood in the Shaker locus from Drosophila, which contains 21 exons spanning 130 kb and generates four different $K^+$ channel proteins through alternative spicing of a single primary transcript (2). Expression of these cDNAs in Xenopus oocytes gives rise to voltage-dependent $K^+$ currents with distinct physiological properties (3). The related Drosophila $K^+$ channel gene Shab also exhibits alternative splicing of a primary transcript, giving rise to two distinct proteins (4).

Therefore, attention focused on the ion channel itself. Three types of ion channel types, classified pharmacologically and electrophysiologically, have been identified, the so-called n, n' and l types. T cells in the peripheral lymphoid tissues for present purposes are characterized into relevant types: $CD4^+CD8^-$, $CD4^-CD8^+$, $CD4^-CD8^-$. The $CD4^+$ $CD8^-$ cells are thought to express approximately 20 n and lchannels per cell and no n channels. And $CD4^-CD8^-$ T cells are believed to express about 20 channels per cell, all three types being represented. In a normal immune response reflecting induction of activity, such as with mitogens, the n channel types are increased upwards of ten fold in the cells that are activated. Thus, normal T cells when stimulated by mitogens, show as a normal immune response elevation in the number of n channels.

Initial original research on the $K^+$ channels resulted in the unequivocal finding that l $K^+$ channel expression is linked to autoimmune disease states. Consequently, assays and treatment regimens and associated aspects of that finding are the subject of a patent application by Cahalan et al., U.S. Ser. No. 07/391,499, filed 6 Mar. 1989. See also the scientific report of this research in Chandy, et al., *European Journal of Immunology* 20, 747–751 (1990).

It is thus a goal in the art to perform experiments with representative models in order to establish whether, and if so how, T-cell activation, that is considered to be the mediator in various disease states, such as various cancers, is linked to $K^+$ channel expression.

Dr. Chandy's group presented initial aspects preliminary to this finding in a poster session in February 1990 (Biophysical Meeting in Baltimore, Md.), and in an abstract submitted in preparation of the 10th International Biophysics Congress to be held 29 Jul. to 3 Aug. 1990 in Vancouver, Canada. See also Chandy et al., *Science* 247, 973 (1990) (12), where inter alia, the sequence of the MK3 gene is disclosed as such. See also Douglass, et al., *J. Immunology* 144, 4841 (June 1990), as well as (7–8 and 28).

The publications and other materials hereof used to illuminate the background of the invention, and the particular cases, to provide additional details respecting its practice are incorporated herein by reference, and for convenience, are numerically referenced of the following text and respectively grouped in the appended bibliography.

SUMMARY OF THE INVENTION

The present invention is grounded in the surprising, and unequivocal finding that the MK3 gene encodes the type n $K^+$ channel in mouse T-lymphocytes. Consequential, further research revealed the finding that functional n $K^+$ channel expression products of encoding DNA of the MK3 gene, or functionally bioactive equivalents, provided the means for developing assays, method and products for use pharmacologically in animals (including not only the murine genus), and homologously in human beings.

Thus, the present invention provides an assay for identifying materials having a modulating effect on n $K^+$ channel expression in a mammal which comprises the steps of: providing an expression system that produces a functional n $K^+$ channel expression product of encoding DNA of the MK3 gene or a functionally bioactive equivalent; contacting the expression system or the product of the expression system or its equivalent with one or more materials to determine its modulating effect on the bioactivity of the product or equivalent and selecting from the materials a candidate or candidates capable of modulating n $K^+$ channel expression.

The selecting step of the assay may preferably measure the capacity of the materials to block the bioactivity effect of the product or its equivalent. In a preferred embodiment, the MK3 gene may comprise a mouse n $K^+$ channel gene. Furthermore, the functionally bioactive equivalent may preferably comprise a functional human n $K^+$ channel expression product. This functionally active bioequivalent, in a preferred embodiment, may comprise a functional homologue of a human n $K^+$ channel expression product, which furthermore may comprise a product of synthetic derivation. In a preferred embodiment, the expression system may comprise a transfectant, the transfectant most preferably comprising a mammalian cell harboring DNA operatively encoding the product or equivalent.

In accordance with another aspect of the present invention, there is provided a method useful to inhibit activation of mammalian of T cells comprising effecting the steps outlined in the above-referenced assay and then contacting the mammalian T cells with the candidates selected in the assay. The contacting step used in the method is preferably accomplished via a composition containing the candidate as an essential component. Most preferably, the contacting is accomplished via administration to a human subject.

In another preferred embodiment, the method useful to inhibit activation of mammalian T cells may also be useful to inhibit tissue graft rejection where the T cells are those of a tissue graft recipient. In another preferred embodiment, the method is useful to screen individuals for the presence of tumorality where the T cells are those of a tumor-suspect individual.

In accordance with another aspect of the present invention, there is provided an assay for diagnosing a diseased state associated with n $K^+$ channel expression mediated T cell activation comprising the steps of: providing T cells containing n $K^+$ channels from a test individual; identifying activated n $K^+$ T cells from among the population of T cells; and measuring the activation of the T cells relative to the total T cell population by measuring n $K^+$ channel expression using labeling means based on a functionally bioactive product of encoding DNA of the MK3 gene or a functionally bioactive equivalent.

In yet another embodiment of the present invention, there is a test kit useful for the detection of the disease state associated with n $K^+$ channel expression mediated T cell activation which comprises structure for receiving and testing a culture of T cells containing n $K^+$ channels from a test individual and means for identifying activated T cells from among the population of T cells of the culture and measuring the relative numbers of type n $K^+$ channels of the cells using labeling means based on a functionally bioactive product of encoding DNA of the MK3 gene or a functionally bioactive equivalent. The present invention is further directed to kits containing associated structure, reagents and means to conduct diagnostic or screening assays.

In yet another embodiment of the present invention, there is provided, for above-disclosed use, DNA (recombinant or cDNA) encoding the MK3 gene product (SEQ ID NO:2) or a functionally bioactive equivalent thereof, and vectors and transfectants operatively harboring same. In a preferred embodiment, the DNA encodes the MK3 gene product (SEQ ID NO:2). In another preferred embodiment, there is provided a transfected cell comprising DNA encoding the MK3 gene product (SEQ ID NO:2) or a functionally bioactive equivalent thereof. In a particularly preferred embodiment, the transfected cell is a mammalian cell. In a further preferred embodiment, there is provided a vector comprising the DNA encoding the MK3 gene product or a functionally bioactive equivalent thereof.

The present invention is further directed to isolates of DNA encoding the MK3 gene product of functionally bioactive equivalent. It is further directed to expression vectors harboring such DNA comprising expression control elements operative in the recombinant host selected for the expression of such DNA and preferably comprising appropriate termination, replication, and other sequences that functionally assist the integration of the expression vector into a recombinant host by transfection, optionally coupled with actual integration into the host's genome.

In respect of the recombinant DNA aspects of the present invention, the technology is applicable directly in all of its aspects, for example: DNA isolate production; including cross-hybridizable DNA isolates; devising expression vectors for them; and producing transfected hosts.

Further, the present invention is directed to the foregoing aspects and all of their associated embodiments as will be represented as equivalents within the skill of those in the art.

BRIEF DESCRIPTION OF THE DRAWINGS

FIGS. 1A–1D depict K$^+$ currents in an outside-out patch from an oocyte injected with MK3 mRNA. The membrane potential was –80 mV, and depolarizing pulses were applied every 45 s. The test potential was changed from –50 to 50 mV in 10 mV increments. B) Peak K$^+$ conductance-voltage relation for the K$^+$ currents shown in A. The line through the points was fitted with the Boltzmann equation:

$$S_K(E) = S_K \text{max}/(1 + \exp[(E_n - E)/k])$$

with parameter values:

$$S_K \text{max} = 3.9 \text{ nS}; E_n = -40.2 \text{ mV}; k = -4.0 \text{ mV}.$$

Activation (C) and inactivation (D) time constants $r_n$ and $r_h$, were obtained by fitting curves through the current data points of similar traces as shown in (A) according to a Hodgkin-Huxley type n$^4$h model:

$$I_{total} = I_K \text{max}[l - \exp(-t/r_n)]^4 \exp(-t/r_h)$$

The points in (C) and (D) represent averages of $r_n$ and $r_h$ obtained from five different patches.

Figure 2B:
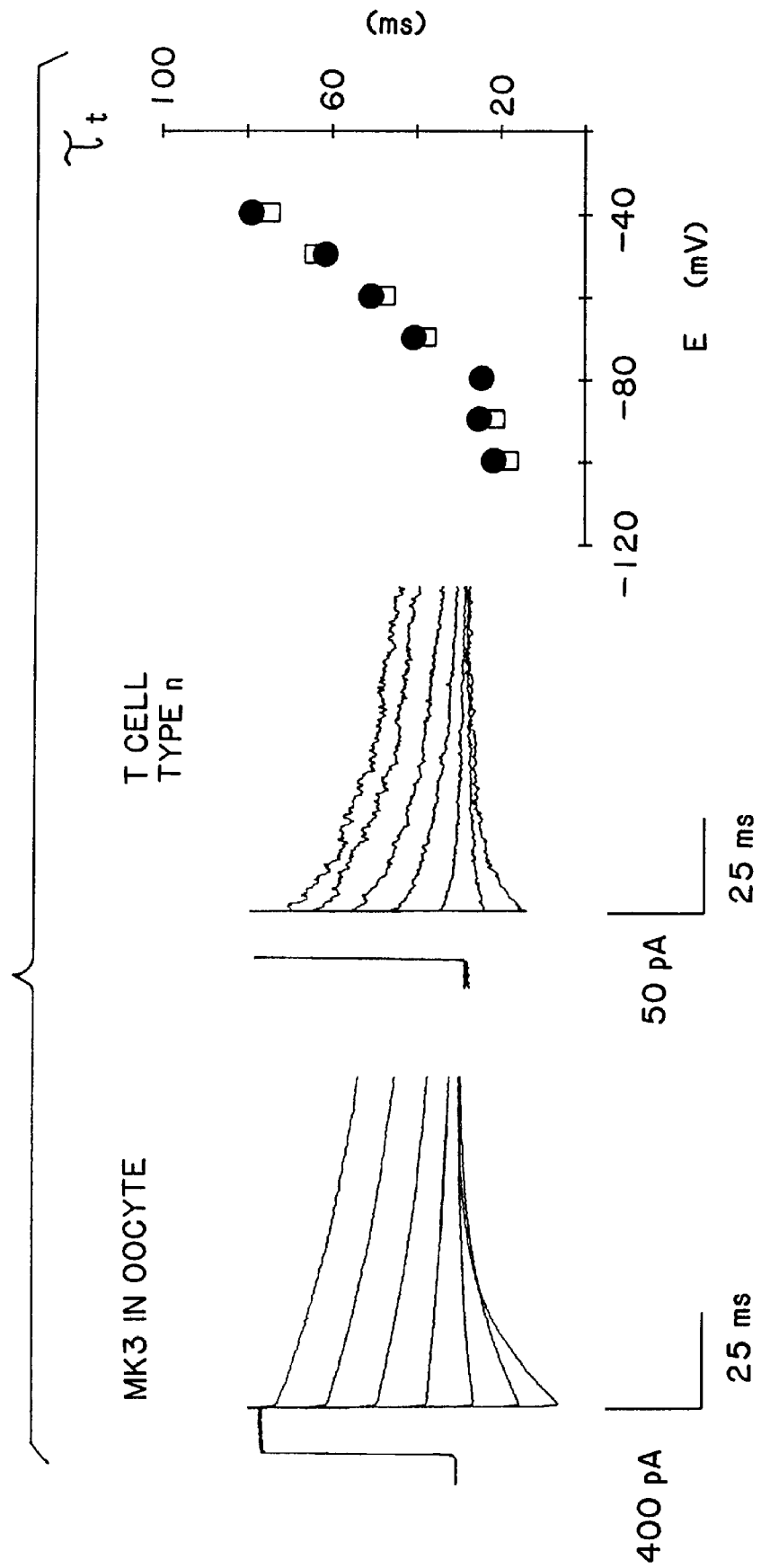
Figure 2C:
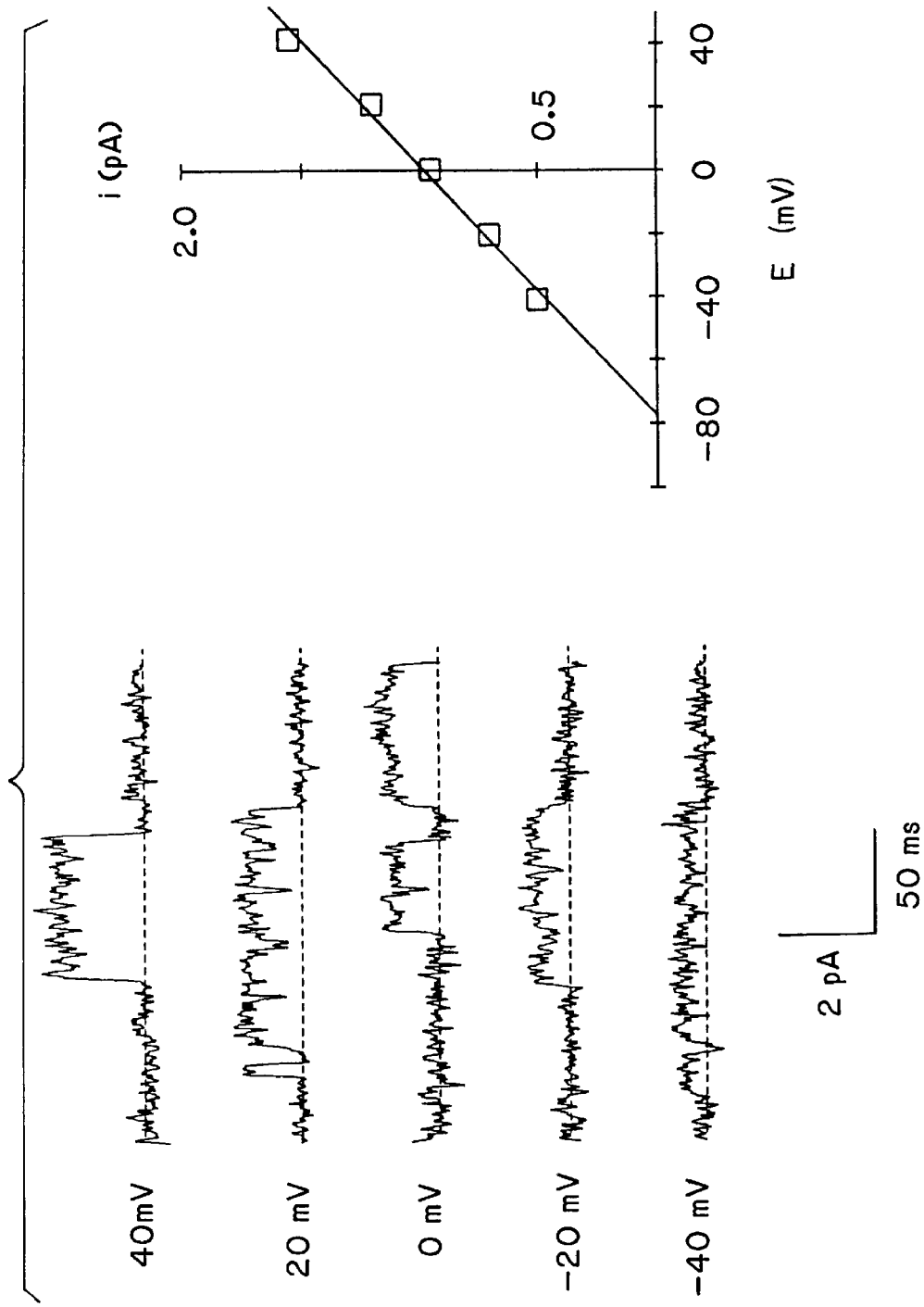

FIGS. 2A–2C provide a comparison of the biophysical properties of MK3 and the type n K$^+$ channel.

FIG. 2A shows cumulative (use-dependent) inactivation of MK3 K$^+$ currents in an outside-out patch from an oocyte injected with MK3 mRNA (left), and of K$^+$ currents obtained from a human peripheral blood lymphocyte (right). Currents were elicited by a train of 6 depolarizing voltage steps to 40 mV once every second from a holding potential of –80 mV. The test pulse duration was 200 ms. The K$^+$ current amplitude decreases substantially during this train of pulses from largest (first) to smallest (last).

FIG. 2B shows the kinetics of deactivation of MK3 K$^+$ currents in an outside-out patch from an oocyte injected with MK3 mRNA (left) and of K$^+$ currents obtained from a human peripheral blood lymphocyte (right). Tail currents were elicited by voltage steps from –100 to –40 mV after a 15 ms depolarizing prepulse to 40 mV. Tail current decay time constants, $r_t$, were fitted with single exponentials and plotted vs. the applied membrane potential, E, during the decay (right). The filled circles represent $r_t$ for MK3, the open squares $r_t$ for the T cell.

FIG. 2C shows single-channel currents of MK3 K$^+$ currents in an outside-out patch from oocyte injected with MK3 mRNA. Left: The membrane potential was held at the potentials indicated on the left side of the current traces. After most of the channels in the patch inactivated, single channel currents of different amplitudes at the different holding potentials could be monitored. On the right side of the figure, the current amplitude produced by the opening of single channels is plotted against the different holding potentials. The slope of the line fitted through the points gives an estimate of 13 pS for the single channel conductance and the line intercepts the voltage axes at –76 mV, close to the calculated reversal potential for K$^+$ ions.

FIGS. 3A–3C provide data relating to the pharmacology of the MK3 K$^+$ channels.

FIG. 3A shows effect of 10, 40 and 160 mM TEA on MK3 K$^+$ currents in an outside-out patch from an oocyte injected with MK3 mRNA. K$^+$ currents were elicited with depolarizing pulses to 40 mV from a holding potential of –80 mV every 45 s before and during treatment with various TEA concentrations. FIG. 3B shows the effect of 3 nM CTX on MK3 K$^+$ currents in another outside-out patch using the same pulse protocol as in FIG. 3A. FIG. 3C gives the dose-response curve of different drugs blocking MK3 K$^+$ current yielding K$_d$s for verapamil, quinine, 4-AP, and TEA of 4 $\mu$M, 40 $\mu$M, 0.4 mM, and 11 mM, respectively.

Figure 4:
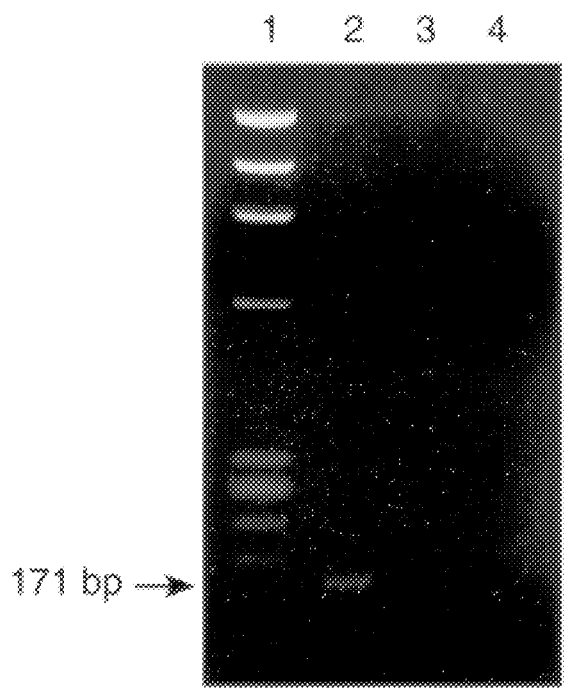

FIG. 4 illustrates the amplification of a 171 bp fragment from EL4 RNA. Lane 1: molecular weight markers, lambda Btt-E1; the 72 bp marker is obscured by the dye band; Lane 2: 171 bp fragment amplified from EL4 RNA; 5 $\mu$l of PCR product was loaded in this lane; Lane 3: EL4 RNA pretreated with RNAse prior to PCR; 20 $\mu$l of PCR product was loaded in this lane; 171 bp fragment not visible.

FIG. 5 graphically depicts chromosomal localization of MK2 and MK3. + indicates the human chromosome is present in at least 80% of the cells; * indicates the human chromosome is present in 50–80% of the cells; d indicates the human chromosome is partially deleted; P and Q indicate just the short or long arms, respectively, of the chromosomes are present. MK2 shows no discordant clones for chromosome 12 while MK3 shows no discordant clones for chromosome 13.

FIG. 6 represents the MK3 nucleotide sequence (SEQ ID NO:1).

DETAILED DESCRIPTION

A. Definitions

By the term "material" herein is meant any entity that is not ordinarily present or functional with respect to type n K$^+$ channels and/or (activated) T cells and that affects same. Thus, the term has a functional definition and includes known, and particularly, unknown entities that are identified and shown herein to have a modulating effect on n K$^+$ channel expression, and/or the associated T-cells.

By the term "modulating effect", or grammatical equivalents, herein is meant both active and passive impact on type n K$^+$ channels and/or T cells. These include, but shall not be construed as limited to, blocking the channel or the function of the channel protein(s), reducing the number of ion channels per cell and use of secondary cell(s) or channel(s) to impact on a primary abnormal cell.

By the term "measuring" in respect of effect of materials on type n K$^+$ channels and/or T cells herein is meant any method known or devised for measuring the impact of a material on said channels/cells. These include, but shall not be construed as limited to, measuring current, measuring membrane potential, measuring K$^+$ flux, such as with radioactive tracers, measuring K$^+$ concentration and measurements of indirect consequences to other receptors, second messengers and/or channels.

By the term "functional" in respect of an n K$^+$ channel expression product herein is meant that that product works for its intended purpose, to wit, that it is bioreactive equivalently as is the direct product of the MK3 gene as such.

The term "functionally bioactive equivalent" herein means that the entity referred to does substantially the same thing in substantially the same way to give substantially the same result as the expression product of the MK3 gene as such.

By the term "expression system" herein is meant matter capable of producing a functional n K$^+$ channel expression product. In preferred embodiments, such systems are microorganisms or cell cultures harboring operatively DNA encoding such functional n K$^+$ channel expression products. "Operative," or grammatical equivalents, means that the respective DNA sequences are operational, that is, work for their intended purposes. Thus, the DNA is preferably contained within expression vectors that are used to transfect recombinantly suitable host cells. The vectors and methods disclosed herein are suitable for use in host cells over a wide range of prokaryotic and eukaryotic organisms. "Transfectants" refers to cells and viruses which have been transfected or transformed with vectors constructed using recombinant DNA techniques, including expression systems including but not limited to, Xenopus and vaccina.

In general, prokaryotes are preferred for cloning of DNA sequences in constructing the vectors useful in the invention. For example, *E. coli* K12 strain 294 (ATCC No. 31446) is particularly useful. Other microbial strains which may be used include *E. coli* strains such as *E. coli* B, and *E. coli* X1776 (ATCC No. 31537). These examples are, of course, intended to be illustrative rather than limiting.

Prokaryotes may also be used for expression. The aforementioned strains, as well as *E. coli* W3110 (F-, lambda-, prototrophic, ATCC No. 27235), bacilli such as *Bacillus subtilus,* and other enterobacteriaceae such as Salmonella typhimurium or Serratia marcestens, and various pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transfected cells. For example, *E. coli* is typically transformed using pBR322, a plasmid derived from an *E. coli* species [Bolivar, et al., *Gene* 2, 95 (1977)]. pBR322 contains genes for ampicillin and tetracycline resistance and thus provides easy means for identifying transfected cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems [Chang, et al., *Nature* 275, 617 (1978), Itakura, et al., *Science* 198, 1056 (1977)], Goeddel, et al., *Nature* 281, 544 (1979)] and a tryptophan (trp) promoter system [Goeddel, et al., *Nucleic Acids Res.* 8, 4057 (1980); EPO Appl Publ No. 0036776]. While these are the most commonly used, other microbial promoters have been discovered and utilized, and details concerning their nucleotide sequence have been published, enabling a skilled worker to ligate them functionally with plasmid vectors [Siebenlist, et al., *Cell* 20, 269 (1980)].

In addition to prokaryotes, eukaryotic microbes, such as yeast cultures may also be used. *Saccharomyces cerevisiae,* or common baker's yeast is commonly used among eukaryotic microorganisms, although a number of other strains are commonly available, such as Pichia strains, for example.

Suitable promoting sequences in yeast vectors include the promoters for 3-phosphoglycerate kinase [[Hitzeman, et al., *J. Biol. Chem.* 255, 12073 (1980)] or other glycolytic enzymes [Hess, et al., *J. Adv. Enzyme Reg.* 7, 149 (1968) and Holland, et al., *Biochemistry* 17, 4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephonsphate isomerase, phosphoglucose isomerase, and glucokinase. In constructing suitable expression plasmids, the termination sequences associated with these genes are also ligated into the expression vector 3' of the sequences desired to be expressed to provide polyadenylation of the mRNA and termination. Other promoters, which have the additional advantage of transcription controlled by growth conditions are the promoter regions for the methanol-regulated alcohol oxidase I (AOX1) gene of Pichia pastoris (see EPA Publn. No. 183071), alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast compatible promoter, origin of replication and termination sequences is suitable.

In addition to microorganisms, cultures of cells derived from multicellular organisms may also be workable, whether from vertebrate or invertebrate culture. However interest has been greatest in vertebrate cells, and propagation of vertebrate cells in culture (tissue culture) has become a common procedure in recent years [*Tissue Culture,* Academic Press, Kruse and Patterson, editors (1973)]. Examples of such useful host cell lines are VERO and HeLa cells, Chinese hamster ovary (CHO) cell lines, and W138, BHK, COS-7 and MDCK cell lines. One such useful cell line is a CHO line, CHO-K1 ATCCF No. CCL 61. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication [Fiers, et al., *Nature* 273, 113 (1978)]. Smaller or larger SV40 fragments may also be used, provided there is included the approximately 250 bp sequence extending from the Hind III site toward the BgI I site located in the viral origin of replication. Further it is also possible, and often desirable, to utilize promoter or control sequences ordinarily associated with the desired gene sequence, provided such sequences are compatible with host cell systems.

An origin of replication may be provided either by construction of the vector to include an exogenous origin, such as may be derived from SV40 or other viral (e.g., Polyoma, Adeno, VSV, BPV, etc.) source, or may be provided by the host cell chromosomal replication mechanism. If the vector is integrated into the host cell chromosomes, the latter is often sufficient.

If cells without formidable cell membrane barriers are used as host cells, transfection is carried out by the calcium phosphate precipitation method as described by Graham and Van der Eb, [*Virology* 52, 456 (1973)]. However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F. N., et al., [*Proc. Natl. Acad. Sci.* (U.S.A.) 69, 2110 (1972)].

Construction of suitable vectors containing the desired coding and control sequences employ standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 $\mu$l plasmid or DNA fragment is used with about 1 unit of enzyme in about 20 $\mu$l of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° C. with 10 units of Polymerase I (Klenow), phenol-chloroform extracted, and ethanol precipitated.

Size separation of the cleaved fragments is performed using, for example, 6 percent polyacrylamide gel described by Goeddel, D., et al., *Nucleic Acids Res.* 8, 4057 (1980).

For ligation, approximately equimolar amounts of the desired components, suitable end tailored to provide correct matching are treated with about 10 units T4 DNA ligase per 0.5 $\mu$g DNA. (When cleaved vectors are used as components, it may be useful to prevent religation of the cleaved vector by pretreatment with bacterial alkaline phosphatase.)

For analysis to confirm correct sequences in plasmids constructed, the ligation mixture may be used to transform *E. coli* K12 strain 294 (ATCC No. 31446), and successful transformants selected by ampicillin or tetracycline resistance where appropriate. Plasmids from the transformants are prepared, analyzed by restriction and/or sequenced by the method of Messing, et al., *Nucleic Acids Res.* 9, 309 (1981) or by the method of Maxam, et al., *Methods of Enzymology* 65, 499 (1980).

In addition to the above discussion and the various references to existing literature teachings, reference is made to standard textbooks of molecular biology that contain definitions and methods and means for carrying out basic techniques encompassed by the present invention. See, for example, Maniatis, et al., *Molecular Cloning: A Laboratory Manual,* Cold Spring Harbor Laboratory, New York, 1982 and the various references cited therein. All of the herein-cited publications are by this reference hereby expressly incorporated herein.

The present invention is thus directed to the identification, management, diagnosis and/or control of a disease state including:

(1) use as a prognostic tool, for example, by making reactive antibodies to the type n K$^+$ channels and measuring the numbers thereof, and/or (2) selectively screening for preferably selective modulators and/or blocking materials of type n K$^+$ channels for use as a diagnostic, and/or (3) blocking, retarding, modulating or eliminating selectively type n K$^+$ channels and/or associated T cell response for use as a therapeutic.

Test kits designed to achieve these therapeutic end points are constructed in accord with the skill extant in the art.

B. Preferred Embodiment

The foregoing description and following experimental details set forth the methodology employed initially by the present researchers in identifying, isolating, characterizing and determining the significance of the MK3 gene product (SEQ ID NO:2) in respect of disease states mediated by T-cell activation via n K$^+$ channel expressions. The art-skilled will recognize that by supplying such information for the MK3 gene, as detailed herein, it is not necessary, or perhaps even scientifically advisable, to repeat those details in their endeavors to reproduce this work. Instead, they may choose to employ alternative, reliable and known methods. Thus, they may identify related polypeptides via immuno cross-reactivity to antibodies raised to, for example, its reactive determinant(s). They may synthesize the underlying DNA sequence for deployment within similar or other suitable, operative expression vectors and culture systems. They may use the sequences herein to create probes, preferably from regions at both the N-terminus and C-terminus, to screen genomic libraries in isolating total encoding DNA for deployment as described above. They may use the sequence information herein in cross-hybridization procedures to isolate, characterize and deploy, as above described, DNA encoding related gene products of other species, or DNA encoding related (e.g., gene family) gene products of the same or other species, or to devise DNA for such characterization, use and deployment encoding functionally equivalent gene products of all the above differing in one or more amino acids from the MK3 gene product or in glycosylation patterns or in bounded conformational structure.

Thus, in addition to supplying details actually employed, the present disclosure serves to enable reproduction of the MK3 gene product (SEQ ID NO:2) disclosed and functionally bioactive equivalents, using means within the skill of the art having benefit of the present disclosure. All of such means are included within the enablement and scope of the present invention.

Two approaches were used to establish the molecular identity of the type n K$^+$ channel in T lymphocytes. The first was to compare its biophysical properties with current in an oocyte following injection of MK3 mRNA. Examined were the voltage dependence of opening and closing, conductance properties, and pharmacological sensitivity of the channel encoded by the MK3 gene, and it was found that these properties of the MK3 gene are the same as those of type n K$^+$ channels in both mice and humans (summarized in Table 1).

TABLE I

Comparison of MK3 and type n currents from T cells

| | Gating | | | | Single channel conductance | | | Blockers | | |
|---|---|---|---|---|---|---|---|---|---|---|
| | $V_n$ (mV) | $k_n$ (mV) | $r_h$ at 40 mV (ms) | $r_{tail}$ at −60 Mv (ms) | i (pS) | TEA (mM) | 4-AP (mM) | quinine ($\mu$M) | verapamil ($\mu$M) | CTX ($\mu$M) |
| MK3 | −35 | −6.3 | 250 | 55 | 13 | 11 | 0.4 | 40 | 4 | <1.0 |
| type n (human) | −36 | −4.3 | 178 | 44 | 9, 16 | 8 | 0.19 | 14 | 6 | <1.0 |
| type n (mice) | −36 | −7.3 | 107 | 49 | 12–18 | 10–13 | <0.2 | 4–40 | 4–40 | <1.0 |

PCR was used as a second approach to demonstrate that MK3 is transcribed and expressed in T cells. Using oligonucleotide primers derived from the unique S1-S2 interdomain region of MK3, a 171 bp fragment as amplified from T cell RNA that was predicted from the MK3 sequence (12). Based on this data, it is concluded that MK3 encodes type n K$^+$ channels from lymphocytes.

MK1, MK2 and MK3 share about 70% coding region sequence identity, although their nearby non-coding regions do not share any discernible sequence similarity (12). All three genes have coding regions that are contained in single uninterrupted exons, and comprise a gene family that probably arose by gene duplication from a common ancestor (12). Members of closely related gene families are often located together on a chromosome. To examine whether MK1–3 are organized in this fashion, MK2- and MK3-specific non-coding region probes (12) were used to ascertain the chromosomal location of these two genes. Surprisingly, MK2 and MK3 are present on separate chromosomes, MK2 on human chromosome 12 and MK3 on human chromosome 13. The three isoforms of the alpha subunit of the GABA$_A$ receptor are similarly located on three different chromosomes (26). Retroviral and retrotransposons have been hypothesized to insert processed genes into the eukaryotic genome, giving rise to diverse chromosomal locations for closely related genes (27). However, MK1–3 have introns within the 5' non-coding regions (12), and are not therefore processed. Thus, retroviral or retrotransposon insertion events are unlikely to account for the different chromosomal locations of MK2 and MK3.

Type n K$^+$ channel expression varies during mouse T cell development (1,4). Immature proliferating thymocytes display ~200 type n K$^+$ channels per cell (1), the number decreasing to about 10–20/cell during differentiation into mature quiescent T cells (1,5). Activation of mature T cells results in a 20-fold increase in K$^+$ channel number, the increase being exclusively of type n (3). The molecular mechanisms responsible for these changes in type n K$^+$ channel expression are not understood. Future characterization of the MK3 gene and its regulatory elements during T cell development and activation may clarify these issues.

Lymphocytes express three distinct types of voltage-gated K$^+$ channels according to functional subset, during development and the state of activation (1–6). Several lines of evidence suggest that the type n K$^+$ channel in mouse and human T lymphocytes plays an essential role in T cell proliferation thymocyte subsets and in mature cells following mitogen stimulation (3,4), and K$^+$ channel blockers inhibit mitogen-induced cell division and secretion of interleukin-2 (6–9). In addition, type n channels may underlie K$^+$ efflux during volume regulation in response to hypotonic osmotic challenge (10,11). The gene encoding this channel has not previously been identified.

MK1, MK2 and MK3 comprise a family of Shaker-related K$^+$ channel genes with intronless coding regions (12). Here it is demonstrated that expression of the MK3 coding region in Xenopus oocytes gives rise to voltage-dependent K$^+$ currents of the voltage-gated type n K$^+$ channel. In addition, the polymerase chain reaction amplification procedure (PCR) was used to show that MK3 is expressed in T cells. Probes prepared from the unique 5'non-coding region of MK3 (12) was used to localize MK3 to human chromosome 13.

C. Materials and Methods

1. Construction and Expression of MK3 in Xenopus Oocytes

The MK3 coding region was inserted into the pSP64T cloning vector (13) as follows. MK3 plasmid DNA was cut with BanL, which cuts 9 nucleotides after the ATG initiation codon and 60 nucleotides after the TAA stop codon to generate a 1774 bp fragment containing almost the entire coding region (12). The DNA was filled with Klenow polymerase and ligated to a synthetic oligonucleotide (CACGGTCATAGATCTATGACCGTG) (SEQ ID NO:3) which generated the first 9 nucleotides and contained a BgIII recognition site. The fragment was then cut with BgIII (which does not cut within the coding region) and inserted into the single BgIII size in pSP64T. Minipreps (14) were analyzed for the appropriate orientation by digestion with ScaI, and the construction was verified by double-stranded DNA sequencing by the dideoxy chain termination method (15), using the Sequenase sequencing kit (U.S. Biochemical, Cleveland, Ohio). For transcription the plasmid was linearized by digestion with EcoRI. RNA was transcribed and injected into oocytes as described previously (16).

Electrophysiology. Experiments were carried out on Xenopus oocytes with two-electrode voltage-clamp and patch-clamp techniques (17). All experiments were done at room temperature (22°–26° C.). For this two-electrode voltage-clamp experiments, cells were bathed in oocyte Ringer solution containing: 96 mM NaCl, 1.8 mM CaCl$_2$, 1 mM MgCl$_2$. The pipette solution was 3M KCl. Patch-clamp experiments were carried out under identical conditions in oocytes and in T cells, using a mammalian Ringer solution containing: 160 mM NaCl, 4.5 mM KCl, 2 mM CaCl$_2$, 1 mM MgCl$_2$, 5 mM HEPES; pH 7.4 adjusted with NaOH; 290–320 mosmol. Internal (pipette) solutions contained: 140 mM KF, 2 mM MgCl$_2$, 5 mM HEPES, 11 mM K$_2$-EGTA. Charybdotoxin (CTX) was a generous gift from Drs. Chris Miller (Graduate Department of Biochemistry, Brandeis University, Waltham, Mass.) and Maria Garcia (Merck Institute, Rahway, N.J.).

The patch-clamp amplifier (List L/M-EPC 7, Adams and List Associates, Ltd., Great Neck, N.Y.) was used in the voltage-clamp mode without series resistance compensation. Patch-clamp electrodes were pulled from Accu-fill 90 Micropets (Becton, Dickinson & Co., Parsippany, N.J.) in three stages, coated with Sylgard (Dow Corning Corp., Midland, Mich.) and fire-polished to resistances, measured in the bath, of 2–7M. In all patch-clamp experiments, the command input of the patch-clamp amplifier was controlled by a computer (PDP 11/73) via a digital-analog converter, and membrane currents were recorded at a band-width of 2 kHz. The holding potential was adjusted in all experiments to E=–80 mV. Correction for capacitative currents was achieved by analog subtraction. The amplitude of the $K^+$ current expressed on oocytes after injection of MK3 mRNA decreased significantly during outside-out patch recordings the $K^+$ current amplitude decreased to 53±8% and 34±13% (mean±SEM; n=6) after 10 and 20 min, respectively, compared to the beginning of the recording in each patch. Due to this run-down the potency of all blockers was determined as the reduction of the mean $K^+$ current before and after drug treatment.

2. Oligonucleotide primers

Two oligonucleotide primers were prepared (ChemGenes Corp., Needham, Mass.) from the unique region flanking the loop between the S1 and S2 transmembrane segments of MK3 (12). The upstream and downstream primers were 5'-GGCATTGCCATTGTGTCAGTGC-3' (SEQ ID NO:4) (which spans the S1 transmembrane helix of MK3) and 5'-GAAGCTGGAGGCTCCAGAAGGGG-3' (SEQ ID NO:5) (which is the 3'–5' complement of the unique 3' end of the S1-S2 loop of MK3).

3. Polymerase chain reaction amplification of MK3 from EL4 RNA

Total RNA was isolated from the mouse T cell line EL4 by the guanldinium isothiocyanate method (14), and this was used to generate a random primed cDNA product (18). The 20 $\mu$reaction mixture contained 48 units AMV reverse transcriptase (Life Sciences), 20 units of RNASin (Boehringer Mannheim), 100 pM random hexanucleotide mixture (Boehringer Mannheim Biochemicals, Indianapolis, Ind.), 1 $\mu$g total EL4 RNA, and 1 mM each of dnTP's (GeneAmp Kit, Perkin-Elmer-Cetus, Norwalk, Conn.). In parallel experiments EL4 RNA was pretreated with boiled 3 $\mu$g RNAse A (Sigma, St. Louis) and RNAse H (Pharmacia) for 30 minutes; the reaction was stopped by the addition of 20 units of RNASin and cDNA synthesis was initiated. The cDNA product was then amplified for 40 cycles (annealing temperature 50° C.) with TAQ polymerase (GeneAmp Kit, Perkin-Elmer-Cetus, Norwalk, Conn.). The reaction mixture contained 50 pMoles of each of the primers and 2 $\mu$l of the cDNA template. The amplified product (5–20 11) was then run on a 2.2% agarose gel in TAE buffer.

4. Chromosomal localization

Since the nearby non-coding regions of MK1, MK2 and MK3 do not share any sequence similarity with each other (12), MK3- and MK2-specific probes were generated from the 5'-NCRs of these genes. A 0.9 kb H3/Pst fragment was prepared from the 5'-NCR of MK2 (12), and a 0.7 kb Pst fragment was isolated from the 5'-NCR of MK3 (12). These probes were labeled to a specific activity of $10^9$cpm/$\mu$g by the random primer method (19), and then used for the chromosomal studies. Chromosomal assignments for MK2 and MK3 loci were determined by Southern blot analysis of a panel of 29 human-chinese hamster cell hybrids (20, 21). The hybrids were isolated using a variety of selectable markers (20, 21). All hybrids were characterized cytogenetically by trypan-Giemsa banding (G-banding) and G-11 staining to determine which human chromosomes were retained. The analysis were repeated at the time the cells were harvested for the preparation of DNA. In all cases, twenty metaphase chromosome spreads were examined. The human chromosome content of the hybrids is indicated in FIG. 5. The presence or absence of human-specific restriction fragments detected by probe MK2 or probe MK3 was correlated with the presence of different human chromosomes in the interspecific cell hybrids.

5. MK3 expression in oocytes

Xenopus oocytes express a high density of voltage-activated $K^+$ channels following injection of 70 nl of 0.01 /$\mu$g/$\mu$l MK3 mRNA. With two-electrode voltage clamping, currents in excess of 20 $\mu$A at test potentials of +40 Mv could be observed (not shown). Outside-out patches of oocyte membrane (70 nl of 0.1 $\mu$g/$\mu$l MK3 mRNA injected) were used for measurement of gating kinetics, pharmacological sensitivity, and single channel properties. Reflecting the large currents seen in micro-electrode recordings from the whole oocyte, current magnitudes in patches were large, often representing a thousand channels per patch (840±242$K^+$ channels/patch; mean±SEM; n=11).

6. Voltage-dependence of MK3

The oocyte patch currents were nearly identical to whole-cell $K^+$ currents found in previous studies with human T lymphocytes (6,9,22). For comparison of channel properties, identical solutions at mammalian ionic strength (290-31-mosm/kg) were employed in oocyte patches and in lymphocytes. FIG. 1 illustrates records and analysis of $K^+$ currents from oocytes expressing the MK3 gene product (SEQ ID NO:2). The outward currents appear to represent a single population of $K^+$ channels which become activated at potentials positive to about 50 Mv. Upon depolarization, the channels open with a sigmoid time course, reach a peak within about 10 msec, and then inactivate with time constants in the range 200–400 msec. From the conductance-voltage relation shown in FIG. 1B, the channels are steeply voltage-dependent, with conductances changing e-fold per 4 mV, with a mid-point at –40 mV. These values are also characteristic of $K^+$ currents recorded in the whole-cell configuration from human T cells. Thus, the voltage dependence for $K^+$ channel activation of MK3 currents matches that of type n lymphocyte $K^+$ currents.

7. Activation and inactivation kinetics

Kinetic properties of activation and inactivation are also similar between MK3 currents and n-type currents from lymphocytes. The time course of $K^+$ currents in five oocytes was analyzed using a modified Hodgkin-Huxley kinetic model with activation ($n^4$) and inactivation (j); no particular mechanism for gating is implied.

FIGS. 1C and 1D illustrate $K^+$ channel kinetics of opening and inactivation for the MK3 gene expressed in oocytes. The rates for channel activation and inactivation are similar to those reported previously in human T lymphocytes (22). Channel inactivation, in particular, provides a convenient property to distinguish between diverse types of K⁺ channels. Inactivation of type n lymphocyte channels progresses with a rate in between classically defined A currents, which inactive in less than 100 nsec, and delayed rectifiers which inactivate with time constants slower than 1 sec (see 23). Moreover, inactivation of type n channels accumulates during repetitive depolarizing pulses delivered at 1 Hz, because recovery during the interpulse interval is incomplete.

Both the time course and use dependence of inactivation exhibited by MK3 K⁺ currents expressed in oocytes are similar to those in the lymphocyte, as shown in FIGS. 1D and 2A. Finally, channel closing upon repolarization is similar between type n K⁺ currents and the MK3 gene product expressed in oocytes, as shown in FIG. 2B.

8. Single-channel conductance

Measurements of single-channel conductance further identify MK3 as the gene which encodes the lymphocyte type n K⁺ channel. In an oocyte patch containing many K⁺ channels it is possible to measure single-channel currents by holding the membrane potential at various depolarized levels. As inactivation proceeds, single channel currents eventually can be seen, as illustrated in FIG. 2C. These currents correspond to a single channel conductance of about 13 pS, similar to that reported in human T cells of 9 and 16 pS (22), and in mouse T cells of 13 (2) and 18 pS (1).

9. MK3 and type n K⁺ channels share similar pharmacological properties

Block by pharmacological agents provides a further test for classification of K⁺ channels. Type n K⁺ channels from lymphocytes are sensitive to block by a wide spectrum of agents (6,8,9,22,24) including (in increasing order of potency) tetraethylammonium (TEA) 4-aminopyridine (4-AP), quinine, verapamil, and CTX. Oocyte K⁺ currents following injection of MK3 mRNA exhibit exactly the same pharmacological specificities, as illustrated in FIG. 3. CTX from both sources (C. Miller and M. Garcia) blocked MK3 channels in oocytes, as they do in lymphocytes (24). Half-blocking doses for type n and MK3 currents, summarized in Table 1, are remarkably similar.

10. MK3 is expressed in EL4 T cells

EL4 cells exhibit voltage-gated type n K⁺ channels (~200/cell) together with inward rectifier K⁺ channels (25). Total RNA from these cells was reversed transcribed and analyzed by PCR. We chose to make primers from the loop linking the S1 and S2 transmembrane helices of MK3 since this region has a unique sequence, which distinguishes it from even the closely related MK1 and MK2 genes (12). A 171 bp fragment predicted from the MK3 sequence, was amplified from EL4 RNA (Lane 2 of FIG. 4). To test whether this fragment was derived from EL4 RNA or from possible contaminating genomic DNA, we pretreated EL4 RNA with DNAse-free RNAse A and H (to degrade RNA without affecting DNA), and then performed PCR. We were unable to amplify the 171 bp fragment from RNAse treated EL4 RNA (lane 3 of FIG. 4), indicating that the fragment was derived from the RNA, rather than from any possible genomic DNA contaminant. Collectively, these data support the MK3 expression in EL4 T cells.

11. Chromosomal localization of MK2 and MK3

Based upon Southern blot analysis of a panel of 29 human-Chinese hamster cell hybrids, MK2 was assigned to human chromosome 12 and MK3 was assigned to human chromosome 13. As shown in Table 2, MK2 is 100% concordant with chromosome 12 and MK3 is 100% concordant with chromosome 13.

12. Materials testing

After having identified the n type K⁺ channel expression product or T cells expressing type n K⁺ channels extrinsic materials may be assayed. The effect of the materials on the type n K⁺ channels may preferably be monitored electrophysiologically, for example, by monitoring changes of inactivation properties, or channel closing kinetics, or block, or shift in voltage dependence or activation, or alteration of single channel amplitude, etc. The same procedures may be used to screen a battery of materials on the same expression product or on T cells or on other cells containing type n K⁺ channels. The selectivity of the type n K⁺ channels may be determined by testing the effect of these materials on other ion channel types, for example, type 1 K⁺ channels in T cells. Drugs that modulate type n K⁺ channels selectively are identified as candidates.

13. Preparation of antibodies against type n K⁺ channels

The genes encoding type n K⁺ channels are isolated by standard recombinant DNA techniques such as described in Weir et al., Handbook of Experimental Immunology, Vol. 3 (1986) and other available documents. These genes are used as templates to prepare type n K⁺ channel proteins or peptides, which are used as antigens to prepare antibodies against type n K⁺ channels. A second method for preparing antibodies against type n K⁺ channel is used with cells expressing large numbers of type n K⁺ channels, isolating the cell surface proteins of these cells and using these proteins as antigens for the preparation of antibodies. The antibodies are screened for their ability to (a) effect type n K⁺ channels electrophysiologically, as described supra, or (b) for their ability to destroy cells expressing type n K⁺ channels, when the antibodies are conjugated to a cell toxin, or when the antibodies bind to the cell in the presence of complement, or (c) for the ability of radioisotope-, or dye-, or enzyme-linked antibodies to attach to the cells, attachment being monitored by fluorescence microscopy, by fluorescence cell sorting, by radioactive counting, or by enzyme-linked immunosorbent assays, or other appropriate techniques.

14. Drug and/or antibody testing in autoimmune disease

Materials comprising drugs or antibodies identified by the assays described surpra as being candidates selective for type n K⁺ channels may be tested in vivo for efficacy in appropriate animal models, for example, for their ability to retard the onset and development of immune responses, autoimmune diseases, cell proliferative disorders or reverse autoimmune diseases. The route of administration of the drugs/antibodies can be oral, parental, or via the rectum, and the drug could be administered alone as principals, or in combination with other drugs or antibodies, and at regular intervals or as a single bolus, or as a continuous infusion in standard formations. Drugs or antibodies described supra are also tested in in vitro assays, for example, for their ability to stimulate B cells from autoimmune patients or animal models to secrete autoantibodies.

15. A treatment protocol

Materials identified or candidate by the assays described above are tested for safety in humans as per Federal guidelines. These candidates described supra are administered via standard formulations to patients with diseases, again either orally, parenterally, rectally, alone or in combination, at regular intervals or as a single bolus, or as a continuous infusion, for modulating type n K$^+$ channels in T cells, thereby abrogating their abnormal accessory helper function and impacting on the course of the disease.

Notwithstanding that reference has been made to particular preferred embodiments, it will be further understood that the present invention is not to be construed as limited to such, rather to the lawful scope of the appended claims.

BIBLIOGRAPHY

1. Lewis, R. S., and Cahalan, M. D. (1988), *Science* 239, 771–775.
2. DeCoursey, T. E., Chandy, K. G., Gupta, S., and Cahalan, M. D. (1987), *J. Gen. Physiol.* 89, 379–404.
3. DeCoursey, T. E., Chandy, K. G., Gupta, S., and Cahalan, M. D. (1987), *J. Gen. Physiol.* 89, 405–420.
4. McKinnon, D., and Ceredig, R. (1986), *J. Exp. Med.* 164, 1846–1861.
5. Grissmer, S., Cahalan, M. D., and Chandy, K. G. (1988), *J. Immunol.* 141, 1137–1142.
6. DeCoursey, T. E., Chandy, K. G., Gupta, S. and Cahalan, M. D. (1984), *Nature* 307, 465–468.
7. Chandy, K. G., DeCoursey, T. E., Fischbach, M., Talai, N., Cahalan, M. D., and Gupta, S. (1986), *Science* 233, 1197–1200.
8. Chandy, K. G., DeCoursey, T. E., Cahalan, M. D., McLaughlin, C., and Gupta, S. (1984), *J. Exp. Med.* 160, 369–385.
9. DeCoursey, T. E., Chandy, K. G., Gupta, S. and Cahalan, M. D., (1985), *J. Neuroimmunol.* 10, 71–95.
10. Cahalan, M. D. and Lewis, R. S. (1988), In: *Cell Physiology of Blood*, (Gunn, R., and Parker, J., eds) pp. 208–301. Rockefeller University Press, New York.
11. Grinstein, S., Smith, J. D. (1990). *J. Gen. Physiol.* 95, 97–120.
12. Chandy, K. G., Williams, C. B., Spencer, R. H., Aguilar, B. A., Ghanshani, S., Tempel, B. L., and Gutman, G. A. (1990), *Science* 247, 973–979.
13. Krieg, P. A., and Melton, D. A. (1984), *Nuc. Acids. Res.* 12, 7057–7070.
14. Maniatis, T., Fritsch., Sambrook, J. (1982), *Molecular Cloning a Laboratory Manual,* Cold Spring Harbor Laboratory, Cold Spring Harbor, New York.
15. Sanger, F., Nicklen, S., Coulson, A. R. (1977), *Proc. Natl. Acad. Sci. USA* 74, 5463–5467.
16. Auld, V. J., Goldin, A. L., Krafte, D. S., Marshall, J. J., Dunn, M., Catterall, W. A., Lester, H. A., Davidson, N., and Dunn, R. J. (1988), *Neuron* 1, 449–461.
17. Hamill, O. P., Marty, A., Neher, E., Sakmann, B., and Sigworth, F. J. (1981), *Pflugers Archiv.* 391, 85–100.
18. Krug, M. S., Berger, S. L. (1987), *Methods Enzymol.* 152, 316–325.
19. Feinberg, A. P., Vogelstein, B. (1983), *Anal. Biochem.* 132, 6–13.
20. Cirullo, R. E., Arrendo-Vega, F. X., Smith, M., Wasmuth, J. J. (1983), *Somatic Cell Genetics* 9, 215–233.
21. Overhauser, J., Memahon, J., Wasmuth, J. J. (1987), *Nuc. Acids. Res.* 25, 4617–4627.
22. Cahalan, M. D., Chandy, K. G., DeCoursey, T. E., and Gupta, S. (1985), *J. Physiol.* 358, 197–237.
23. Hille, B. (1984), *Ionic channels of excitable membranes.* Sinauer Associates Inc., Sunderland, Mass.
24. Sands, S. B., Lewis, R. S., and Cahalan, M. D. (1989), *J. Gen. Phsiol.* 93, 1061–1074.
25. Cahalan, M. D., Chandy, K. G., DeCoursey, T. E., Gupta, S., Lewis, R. S., and Sutro, J. (1987), In: *Mechanisms of Lymphocyte Activation and Immune Regulation.* (Gupta, S., and Fauci, A. S., eds) pp. 85–102, Plenum, New York.
26. Buckle, V. J., Fujita, N., Ryder-Cook, A. S., Derry, J. M. J., Barnard, P. J., Lebo, R. V., Schofield, P. R., Seeburg, P. H., Bateson, A. N., Darlison, M. G., Barnard, E. A. (1989), *Neuron* 3, 647–645.
27. Weiner, A. M., Deininger, P. L., Efatratiatis, A. (1986), *Ann. Rev. Biochem.* 55, 631–661.
28. Grissmer, S., Goldin, A. L., Gutman, G. A., Cahalan, M. D., and Chandy, K. G. Abstract: International Biophysical Congress, Vancouver, Canada (Jul., 1990).

What is claimed is:

1. An in vitro assay for identifying materials having a modulating effect on the activity of n $K^+$ channels in a mammal which comprises:

a. providing an expression system that produces a functional n $K^+$ channel expression product, wherein said n $K^+$ channel expression product is the MK3 gene product shown as SEQ ID NO:2;

b. contacting said expression system or said $K^+$ channel expression product with one or more materials to determine its modulating effect on the bioactivity of said $K^+$ channel expression product; and c. selecting from said materials a candidate(s) which modulates the activity of said n $K^+$ channel.

2. The assay according to claim 1, wherein said selecting step comprises measuring the modulating effect on the bioactivity of said $K^+$ channel expression product.

3. The assay according to claim 2, wherein said modulating effect comprises the capacity to block the activity of said $K^+$ channel expression product.

4. The assay according to claim 1, wherein said functional n $K^+$ channel expression product is the sole $K^+$ channel expression product.

5. The assay according to claim 1, wherein said n $K^+$ channel expression product is produced synthetically.

6. The assay according to claim 1, wherein said expression system comprises a transfectant.

7. The assay according to claim 6, wherein said transfectant is a mammalian cell harboring DNA encoding said n $K^+$ channel expression product.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1994 base pairs
        ( B ) TYPE: nucleic acid
        ( C ) STRANDEDNESS: both
        ( D ) TOPOLOGY: linear ( i x ) FEATURE:
        ( A ) NAME/KEY: CDS
        ( B ) LOCATION: 150..1736

( x i ) SEQUENCE DESCRIPTION: SEQ ID NO:1:

```
AGCCGCCGCT  AGGGAAGGAA  AGCACCGCCG  CCTCCGCGC   TCGACCGCCG  CAGCCCTCCA              60

CCCATCACCG  CGCCCACCCT  GCACCGGACC  CCGCAGGAGG  CGGCGCGCGC  ATCCTGCAGA             120

GCCCCGGCCA  CGCCGAGCTG  CCGCCAGAC   ATG  ACC  GTG  GTG  CCC  GGG  GAC  CAC        173
```

|  |  |  |  |  |  |  |  | Met 1 | Thr | Val | Val | Pro 5 | Gly | Asp | His |  |
|---|---|---|---|---|---|---|---|---|---|---|---|---|---|---|---|---|
| CTG | CTG | GAG | CCA | GAG | GCG | GCG | GGA | GGC | GGT | GGC | GGG | GAC | CCG | CCT | CAG | 221 |
| Leu | Leu 10 | Glu | Pro | Glu | Ala | Ala 15 | Gly | Gly | Gly | Gly | Gly 20 | Asp | Pro | Pro | Gln |  |
| GGA | GGC | TGT | GGC | AGT | GGC | GGC | GGC | GGT | GGC | GGC | TGC | GAC | CGC | TAC | GAG | 269 |
| Gly 25 | Gly | Cys | Gly | Ser | Gly 30 | Gly | Gly | Gly | Gly | Gly 35 | Cys | Asp | Arg | Tyr | Glu 40 |  |
| CCA | CTG | CCA | CCC | GCG | CTG | CCC | GCC | GCG | GGC | GAG | CAA | GAT | TGC | TGC | GGC | 317 |
| Pro | Leu | Pro | Pro | Ala 45 | Leu | Pro | Ala | Ala | Gly 50 | Glu | Gln | Asp | Cys | Cys 55 | Gly |  |
| GAG | CGT | GTG | GTC | ATC | AAC | ATC | TCC | GGG | CTG | CGC | TTC | GAG | ACG | CAG | CTC | 365 |
| Glu | Arg | Val | Val 60 | Ile | Asn | Ile | Ser | Gly 65 | Leu | Arg | Phe | Glu | Thr 70 | Gln | Leu |  |
| AAG | ACC | CTC | TGC | CAG | TTC | CCC | GAG | ACA | CTG | CTG | GGC | GAC | CCC | AAG | CGG | 413 |
| Lys | Thr | Leu 75 | Cys | Gln | Phe | Pro | Glu 80 | Thr | Leu | Leu | Gly | Asp 85 | Pro | Lys | Arg |  |
| CGC | ATG | CGG | TAC | TTT | GAC | CCA | CTC | CGC | AAT | GAG | TAC | TTC | TTC | GAC | CGC | 461 |
| Arg | Met 90 | Arg | Tyr | Phe | Asp | Pro 95 | Leu | Arg | Asn | Glu | Tyr 100 | Phe | Phe | Asp | Arg |  |
| AAC | CGA | CCC | AGC | TTC | GAC | GCC | ATC | CTC | TAC | TAC | TAC | CAG | TCC | GGG | GGC | 509 |
| Asn 105 | Arg | Pro | Ser | Phe | Asp 110 | Ala | Ile | Leu | Tyr | Tyr 115 | Tyr | Gln | Ser | Gly | Gly 120 |  |
| CGC | ATT | CGC | CGG | CCG | GTC | AAC | GTG | CCC | ATC | GAC | ATC | TTC | TCC | GAG | GAG | 557 |
| Arg | Ile | Arg | Arg 125 | Pro | Val | Asn | Val | Pro 130 | Ile | Asp | Ile | Phe | Ser 135 | Glu | Glu |  |
| ATC | CGC | TTT | TAC | CAG | CTG | GGT | GAG | GAG | GCC | ATG | GAA | AAG | TTC | CGT | GAG | 605 |
| Ile | Arg | Phe | Tyr 140 | Gln | Leu | Gly | Glu | Glu 145 | Ala | Met | Glu | Lys | Phe 150 | Arg | Glu |  |
| GAT | GAG | GGC | TTC | CTG | CGG | GAG | GAG | GAG | CGA | CCC | CTG | CCC | CGC | CGT | GAC | 653 |
| Asp | Glu | Gly | Phe 155 | Leu | Arg | Glu | Glu | Glu 160 | Arg | Pro | Leu | Pro | Arg 165 | Arg | Asp |  |
| TTC | CAG | CGC | CAG | GTG | TGG | CTG | CTC | TTC | GAA | TAT | CCG | GAG | AGC | TCC | GGG | 701 |
| Phe | Gln | Arg 170 | Gln | Val | Trp | Leu | Leu 175 | Phe | Glu | Tyr | Pro | Glu 180 | Ser | Ser | Gly |  |
| CCG | GCC | CGG | GGC | ATT | GCC | ATT | GTG | TCA | GTG | CTG | GTC | ATT | CTC | ATC | TCC | 749 |
| Pro 185 | Ala | Arg | Gly | Ile | Ala 190 | Ile | Val | Ser | Val | Leu 195 | Val | Ile | Leu | Ile | Ser 200 |  |
| ATT | GTC | ATC | TTC | TGC | TTG | GAG | ACG | CTT | CCC | GAG | TTT | CGC | GAT | GAG | AAA | 797 |
| Ile | Val | Ile | Phe | Cys 205 | Leu | Glu | Thr | Leu | Pro 210 | Glu | Phe | Arg | Asp | Glu 215 | Lys |  |
| GAC | TAT | CCC | GCC | TCC | CCG | TCG | CAG | GAC | GTG | TTT | GAG | GCT | GCC | AAC | AAC | 845 |
| Asp | Tyr | Pro | Ala 220 | Ser | Pro | Ser | Gln | Asp 225 | Val | Phe | Glu | Ala | Ala 230 | Asn | Asn |  |
| AGC | ACG | TCG | GGG | GCC | CCT | TCT | GGA | GCC | TCC | AGC | TTC | TCG | GAC | CCC | TTC | 893 |
| Ser | Thr | Ser 235 | Gly | Ala | Pro | Ser | Gly 240 | Ala | Ser | Ser | Phe | Ser 245 | Asp | Pro | Phe |  |
| TTC | GTG | GTG | GAG | ACC | TTG | TGC | ATC | ATC | TGG | TTC | TCC | TTT | GAG | CTT | CTG | 941 |
| Phe | Val | Val 250 | Glu | Thr | Leu | Cys | Ile 255 | Ile | Trp | Phe | Ser | Phe 260 | Glu | Leu | Leu |  |
| GTG | CGG | TTC | TTT | GCT | TGC | CCC | AGT | AAA | GCC | ACC | TTC | TCC | AGA | AAT | ATC | 989 |
| Val | Arg 265 | Phe | Phe | Ala | Cys | Pro 270 | Ser | Lys | Ala | Thr | Phe 275 | Ser | Arg | Asn | Ile 280 |  |
| ATG | AAC | TTG | ATA | GAC | ATT | GTG | GCC | ATC | ATT | CCT | TAT | TTT | ATC | ACT | CTG | 1037 |
| Met | Asn | Leu | Ile | Asp 285 | Ile | Val | Ala | Ile | Ile 290 | Pro | Tyr | Phe | Ile | Thr 295 | Leu |  |
| GGC | ACT | GAG | CTG | GCT | GAA | CGA | CAA | GGT | AAT | GGG | CAG | CAG | GCC | ATG | TCG | 1085 |
| Gly | Thr | Glu | Leu 300 | Ala | Glu | Arg | Gln | Gly 305 | Asn | Gly | Gln | Gln | Ala 310 | Met | Ser |  |
| CTG | GCC | ATC | CTA | AGA | GTC | ATC | CGC | CTA | GTA | AGG | GTT | TTC | CGC | ATC | TTC | 1133 |

|   |   |   |   |   |   |   |   |   |   |   |   |   |   |   |
|---|---|---|---|---|---|---|---|---|---|---|---|---|---|---|
| Leu | Ala | Ile | Leu | Arg | Val | Ile | Arg | Leu | Val | Arg | Val | Phe | Arg | Ile | Phe |
|   |   | 315 |   |   |   | 320 |   |   |   |   |   | 325 |   |   |   |

| AAG | CTC | TCC | CGC | CAT | TCT | AAG | GGG | CTG | CAG | ATC | CTA | GGA | CAG | ACG | CTG | 1181 |
|---|---|---|---|---|---|---|---|---|---|---|---|---|---|---|---|---|
| Lys | Leu | Ser | Arg | His | Ser | Lys | Gly | Leu | Gln | Ile | Leu | Gly | Gln | Thr | Leu |   |
|   | 330 |   |   |   |   | 335 |   |   |   |   | 340 |   |   |   |   |   |

| AAG | GCT | TCC | ATG | CGG | GAG | CTG | GGG | CTG | CTC | ATA | TTC | TTC | CTC | TTC | ATT | 1229 |
|---|---|---|---|---|---|---|---|---|---|---|---|---|---|---|---|---|
| Lys | Ala | Ser | Met | Arg | Glu | Leu | Gly | Leu | Leu | Ile | Phe | Phe | Leu | Phe | Ile |   |
| 345 |   |   |   |   | 350 |   |   |   |   | 355 |   |   |   |   | 360 |   |

| GGG | GTC | ATC | CTT | TTC | TCC | AGT | GCA | GCT | TAC | TTT | GCT | GAG | GCA | GAC | GAC | 1277 |
|---|---|---|---|---|---|---|---|---|---|---|---|---|---|---|---|---|
| Gly | Val | Ile | Leu | Phe | Ser | Ser | Ala | Ala | Tyr | Phe | Ala | Glu | Ala | Asp | Asp |   |
|   |   |   |   | 365 |   |   |   |   | 370 |   |   |   |   | 375 |   |   |

| CCT | TCT | TCG | GGT | TTT | AAC | AGT | ATC | CCG | GAT | GCC | TTC | TGG | TGG | GCA | GTA | 1325 |
|---|---|---|---|---|---|---|---|---|---|---|---|---|---|---|---|---|
| Pro | Ser | Ser | Gly | Phe | Asn | Ser | Ile | Pro | Asp | Ala | Phe | Trp | Trp | Ala | Val |   |
|   |   |   | 380 |   |   |   |   | 385 |   |   |   |   | 390 |   |   |   |

| GTA | ACC | ATG | ACA | ACT | GTT | GGT | TAT | GGT | GAT | ATG | CAC | CCA | GTG | ACC | ATA | 1373 |
|---|---|---|---|---|---|---|---|---|---|---|---|---|---|---|---|---|
| Val | Thr | Met | Thr | Thr | Val | Gly | Tyr | Gly | Asp | Met | His | Pro | Val | Thr | Ile |   |
|   |   | 395 |   |   |   |   | 400 |   |   |   |   | 405 |   |   |   |   |

| GGA | GGC | AAG | ATT | GTG | GGC | TCT | CTT | TGT | GCC | ATC | GCA | GGT | GTC | TTG | ACC | 1421 |
|---|---|---|---|---|---|---|---|---|---|---|---|---|---|---|---|---|
| Gly | Gly | Lys | Ile | Val | Gly | Ser | Leu | Cys | Ala | Ile | Ala | Gly | Val | Leu | Thr |   |
|   |   | 410 |   |   |   |   | 415 |   |   |   |   | 420 |   |   |   |   |

| ATT | GCA | TTG | CCA | GTT | CCT | GTG | ATT | GTT | TCC | AAC | TTC | AAC | TAC | TTC | TAC | 1469 |
|---|---|---|---|---|---|---|---|---|---|---|---|---|---|---|---|---|
| Ile | Ala | Leu | Pro | Val | Pro | Val | Ile | Val | Ser | Asn | Phe | Asn | Tyr | Phe | Tyr |   |
| 425 |   |   |   |   | 430 |   |   |   |   | 435 |   |   |   |   | 440 |   |

| CAC | CGG | GAG | ACA | GAA | GGG | GAA | GAG | CAA | GCC | CAG | TAC | ATG | CAC | GTG | GGC | 1517 |
|---|---|---|---|---|---|---|---|---|---|---|---|---|---|---|---|---|
| His | Arg | Glu | Thr | Glu | Gly | Glu | Glu | Gln | Ala | Gln | Tyr | Met | His | Val | Gly |   |
|   |   |   |   | 445 |   |   |   |   | 450 |   |   |   |   | 455 |   |   |

| AGT | TGC | CAG | CAC | CTC | TCC | TCT | TCA | GCC | GAG | GAG | CTC | CGA | AAA | GCC | CGG | 1565 |
|---|---|---|---|---|---|---|---|---|---|---|---|---|---|---|---|---|
| Ser | Cys | Gln | His | Leu | Ser | Ser | Ser | Ala | Glu | Glu | Leu | Arg | Lys | Ala | Arg |   |
|   |   |   | 460 |   |   |   |   | 465 |   |   |   |   | 470 |   |   |   |

| AGT | AAC | TCC | ACT | CTG | AGT | AAG | TCG | GAG | TAT | ATG | GTG | ATC | GAA | GAG | GGG | 1613 |
|---|---|---|---|---|---|---|---|---|---|---|---|---|---|---|---|---|
| Ser | Asn | Ser | Thr | Leu | Ser | Lys | Ser | Glu | Tyr | Met | Val | Ile | Glu | Glu | Gly |   |
|   |   | 475 |   |   |   |   | 480 |   |   |   |   | 485 |   |   |   |   |

| GGT | ATG | AAC | CAG | AGC | GCC | TTC | CCG | CAG | ACC | CCC | TTC | AAA | ACG | GGC | AAC | 1661 |
|---|---|---|---|---|---|---|---|---|---|---|---|---|---|---|---|---|
| Gly | Met | Asn | Gln | Ser | Ala | Phe | Pro | Gln | Thr | Pro | Phe | Lys | Thr | Gly | Asn |   |
|   | 490 |   |   |   |   | 495 |   |   |   |   | 500 |   |   |   |   |   |

| TCC | ACA | GCC | ACT | TGC | ACC | ACG | AAC | AAT | AAC | CCC | AAC | TCC | TGT | GTC | AAC | 1709 |
|---|---|---|---|---|---|---|---|---|---|---|---|---|---|---|---|---|
| Ser | Thr | Ala | Thr | Cys | Thr | Thr | Asn | Asn | Asn | Pro | Asn | Ser | Cys | Val | Asn |   |
| 505 |   |   |   |   | 510 |   |   |   |   | 515 |   |   |   |   | 520 |   |

| ATC | AAG | AAG | ATA | TTC | ACT | GAT | GTC | TAATATGA | TACGGTTGCC | AATTCTGTGC | 1763 |
|---|---|---|---|---|---|---|---|---|---|---|---|
| Ile | Lys | Lys | Ile | Phe | Thr | Asp | Val |   |   |   |   |
|   |   |   |   | 525 |   |   |   |   |   |   |   |

| CCAGTATTGT | GTGGAACATG | CCCCCTTGGT | CTGTGTATGC | CCTTGATTTA | TACATTTCCA | 1823 |
|---|---|---|---|---|---|---|
| GACCACTCAT | CAAGGAAAGT | ACAAGAAGTG | AGGAAGCACA | CTTCATTCTC | CCTATTGCTT | 1883 |
| CATACTGAAA | CAGGTGCCTG | TTTTTGCAAG | TGGGCTGCAT | TCTCTCAGCT | CTTTTTTTCT | 1943 |
| CTCTCTCCCT | GTCTCTTAAT | TTTGTGACCA | ACAAACTTAC | ATTAAGCGTG | G | 1994 |

( 2 ) INFORMATION FOR SEQ ID NO:2:

( i ) SEQUENCE CHARACTERISTICS:
        ( A ) LENGTH: 528 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|   |   |   |   |   |   |   |   |   |   |   |   |   |   |   |
|---|---|---|---|---|---|---|---|---|---|---|---|---|---|---|
| Met | Thr | Val | Val | Pro | Gly | Asp | His | Leu | Leu | Glu | Pro | Glu | Ala | Ala | Gly |
| 1 |   |   |   | 5 |   |   |   |   | 10 |   |   |   |   | 15 |   |
| Gly | Gly | Gly | Gly | Asp | Pro | Pro | Gln | Gly | Gly | Cys | Gly | Ser | Gly | Gly | Gly |
|   |   |   | 20 |   |   |   |   | 25 |   |   |   |   | 30 |   |   |

```
Gly Gly Gly Cys Asp Arg Tyr Glu Pro Leu Pro Pro Ala Leu Pro Ala
         35                  40                 45
Ala Gly Glu Gln Asp Cys Cys Gly Glu Arg Val Val Ile Asn Ile Ser
         50              55                 60
Gly Leu Arg Phe Glu Thr Gln Leu Lys Thr Leu Cys Gln Phe Pro Glu
 65              70                  75                      80
Thr Leu Leu Gly Asp Pro Lys Arg Met Arg Tyr Phe Asp Pro Leu
                 85                  90                  95
Arg Asn Glu Tyr Phe Phe Asp Arg Asn Arg Pro Ser Phe Asp Ala Ile
             100             105                 110
Leu Tyr Tyr Tyr Gln Ser Gly Arg Ile Arg Arg Pro Val Asn Val
             115             120             125
Pro Ile Asp Ile Phe Ser Glu Glu Ile Arg Phe Tyr Gln Leu Gly Glu
     130              135                 140
Glu Ala Met Glu Lys Phe Arg Glu Asp Glu Gly Phe Leu Arg Glu Glu
145                 150             155                     160
Glu Arg Pro Leu Pro Arg Arg Asp Phe Gln Arg Gln Val Trp Leu Leu
                 165             170                 175
Phe Glu Tyr Pro Glu Ser Ser Gly Pro Ala Arg Gly Ile Ala Ile Val
             180             185                 190
Ser Val Leu Val Ile Leu Ile Ser Ile Val Ile Phe Cys Leu Glu Thr
             195             200                 205
Leu Pro Glu Phe Arg Asp Glu Lys Asp Tyr Pro Ala Ser Pro Ser Gln
         210             215                 220
Asp Val Phe Glu Ala Ala Asn Asn Ser Thr Ser Gly Ala Pro Ser Gly
225             230                 235                     240
Ala Ser Ser Phe Ser Asp Pro Phe Phe Val Glu Thr Leu Cys Ile
                 245             250                 255
Ile Trp Phe Ser Phe Glu Leu Leu Val Arg Phe Phe Ala Cys Pro Ser
                 260             265                 270
Lys Ala Thr Phe Ser Arg Asn Ile Met Asn Leu Ile Asp Ile Val Ala
         275             280                 285
Ile Ile Pro Tyr Phe Ile Thr Leu Gly Thr Glu Leu Ala Glu Arg Gln
     290             295                 300
Gly Asn Gly Gln Gln Ala Met Ser Leu Ala Ile Leu Arg Val Ile Arg
305             310                 315                     320
Leu Val Arg Val Phe Arg Ile Phe Lys Leu Ser Arg His Ser Lys Gly
                 325             330                 335
Leu Gln Ile Leu Gly Gln Thr Leu Lys Ala Ser Met Arg Glu Leu Gly
             340             345                 350
Leu Leu Ile Phe Phe Leu Phe Ile Gly Val Ile Leu Phe Ser Ser Ala
             355             360                 365
Ala Tyr Phe Ala Glu Ala Asp Asp Pro Ser Ser Gly Phe Asn Ser Ile
     370             375                 380
Pro Asp Ala Phe Trp Trp Ala Val Val Thr Met Thr Thr Val Gly Tyr
385             390                 395                     400
Gly Asp Met His Pro Val Thr Ile Gly Gly Lys Ile Val Gly Ser Leu
                 405             410                 415
Cys Ala Ile Ala Gly Val Leu Thr Ile Ala Leu Pro Val Pro Val Ile
             420             425                 430
Val Ser Asn Phe Asn Tyr Phe Tyr His Arg Glu Thr Glu Gly Glu Glu
         435             440                 445
Gln Ala Gln Tyr Met His Val Gly Ser Cys Gln His Leu Ser Ser Ser
```

-continued

| | | | | | | | | | | | | | | | |
|---|---|---|---|---|---|---|---|---|---|---|---|---|---|---|---|
| | 450 | | | | | 455 | | | | | 460 | | | | |
| Ala | Glu | Glu | Leu | Arg | Lys | Ala | Arg | Ser | Asn | Ser | Thr | Leu | Ser | Lys | Ser |
| 465 | | | | | 470 | | | | | 475 | | | | | 480 |
| Glu | Tyr | Met | Val | Ile | Glu | Glu | Gly | Gly | Met | Asn | Gln | Ser | Ala | Phe | Pro |
| | | | | 485 | | | | | 490 | | | | | 495 | |
| Gln | Thr | Pro | Phe | Lys | Thr | Gly | Asn | Ser | Thr | Ala | Thr | Cys | Thr | Thr | Asn |
| | | | 500 | | | | | 505 | | | | | 510 | | |
| Asn | Asn | Pro | Asn | Ser | Cys | Val | Asn | Ile | Lys | Lys | Ile | Phe | Thr | Asp | Val |
| | | 515 | | | | | 520 | | | | | 525 | | | |

( 2 ) INFORMATION FOR SEQ ID NO:3:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:3:

CACGGTCATA GATCTATGAC CGTG 24

( 2 ) INFORMATION FOR SEQ ID NO:4:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:4:

GGCATTGCCA TTGTGTCAGT GC 22

( 2 ) INFORMATION FOR SEQ ID NO:5:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:5:

GAAGCTGGAG GCTCCAGAAG GGG 23